(12) United States Patent
Sommerlade et al.

(10) Patent No.: US 7,439,401 B2
(45) Date of Patent: Oct. 21, 2008

(54) PROCESS FOR PREPARING ACYLPHOSPHANES AND DERIVATIVES THEREOF

(75) Inventors: Reinhard H. Sommerlade, Neuenburg am Rhein (DE); Souâd Boulmaâz, Birsfelden (CH); Jean-Pierre Wolf, Maisprach (CH); Jens Geier, Wuppertal (DE); Hansjörg Grützmacher, Dielsdorf (DE); Markus Scherer, Beromünster (CH); Hartmut Schönberg, Kilchberg (CH); Daniel Stein, Seelze (DE); Peter Murer, Allschwil (CH); Stephan Burkhardt, Gelterkinden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 79 days.

(21) Appl. No.: 10/564,711

(22) PCT Filed: Jul. 9, 2004

(86) PCT No.: PCT/EP2004/051427

§ 371 (c)(1),
(2), (4) Date: May 3, 2006

(87) PCT Pub. No.: WO2005/014605

PCT Pub. Date: Feb. 17, 2005

(65) Prior Publication Data

US 2006/0247436 A1    Nov. 2, 2006

(30) Foreign Application Priority Data

Jul. 18, 2003   (EP)   ................... 03405551

(51) Int. Cl.
*C07F 9/02*   (2006.01)
(52) U.S. Cl. ............................. 568/14; 568/10; 568/15; 568/17
(58) Field of Classification Search ........................ None
See application file for complete search history.

(56) References Cited

U.S. PATENT DOCUMENTS

| | | | |
|---|---|---|---|
| 6,399,805 B2 * | 6/2002 | Wolf et al. | 556/405 |
| 6,888,031 B1 | 5/2005 | Leppard et al. | 568/14 |
| 2005/0028027 A1 | 2/2005 | Kroening et al. | 714/6 |
| 2006/0229469 A1 * | 10/2006 | Huttenloch et al. | 562/876 |

FOREIGN PATENT DOCUMENTS

| | | |
|---|---|---|
| CN | 1486986 * | 4/2004 |
| EP | 0 040 721 | 5/1981 |
| WO | 00/32612 | 6/2000 |

OTHER PUBLICATIONS

Veits et al., Russian Journal of General Chemistry (Translation of Zhurnal Obshchei Khimii) (2000), 70(8), 1237-1239.*
Derwent Abst. No. 1981-91349D [50] of EP 0 040 721.
F. Pass et al., Monatshefte Fur Chemie, Vo. 90, 1959, pp. 148-156 and English language abstract thereof.
K. Issleib et al. Che. Ber.vol. 92, (1959), pp. 3183-3189 and English language abstract thereof.

* cited by examiner

*Primary Examiner*—Karl J Puttlitz
(74) *Attorney, Agent, or Firm*—Joseph C. Suhadolnik

(57) ABSTRACT

The present invention relates to a new, selective process for the preparation of mono- and bisacylphosphanes of formula (I) n and m are each independently of the other 1 or 2; $R_1$, if n=1, is e.g. phenyl $R_1$, if n=2, is e.g. $C_1$-$C_{18}$alkylene or phenylene; $R_2$ is e. g. $C_1$-$C_{18}$alkyl, phenyl or substituted phenyl; $R_3$ is e. g. $C_1$-$C_{18}$alkyl, by (1) reacting a phosphorous halide of formula IIa or a phosphorous halide oxide of formula (IIb) or a phosphorous halide sulfide of formula (IIc) with an alkali metal in a solvent in the presence of a proton source; (2) subsequent reaction with m acid halides of formula (III) An oxidation step may follow to obtain mono- and bisacylphosphane oxides or mono- and bisacylphosphane sulfides.

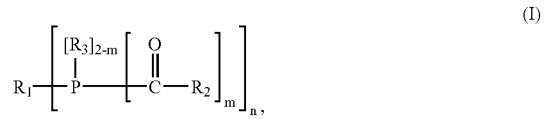

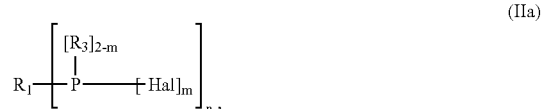

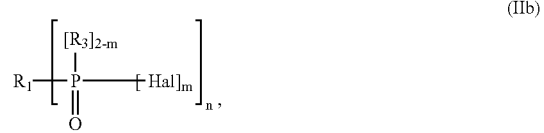

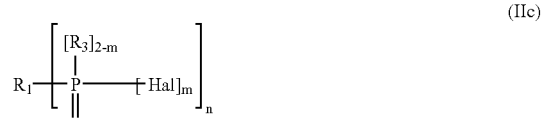

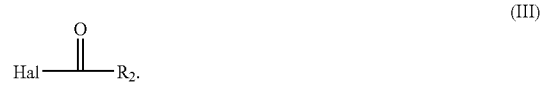

19 Claims, No Drawings

PROCESS FOR PREPARING ACYLPHOSPHANES AND DERIVATIVES THEREOF

The present invention relates to a new, selective process for the preparation of mono- and bisacylphosphanes, mono- and bisacylphosphane oxides or mono- and bisacylphosphane sulfides.

The European Patent Publication EP1 135 399 B1 describes a process for the preparation of mono- and bisacyiphosphanes, of mono- and bisacylphosphane oxides and of mono- and bisacyiphosphane sulfides, which process comprises first reacting organic P-monohalogeno-phosphanes or P,P-dihalogenophosphanes or mixtures thereof, with an alkali metal or magnesium in combination with lithium, where appropriate in the presence of a catalyst, and then carrying out the reaction with add halides and, in the case of the process for the preparation of oxides, carrying out an oxidation step and, in the case of the preparation of sulfides, reacting the phosphanes so obtained with sulfur. The reaction is usefully carried out in a solvent. The solvent used may be, in particular, ethers which are liquid at normal pressure and room temperature. Examples thereof are dimethyl ether, diethyl ether, methyl-propyl ether, 1,2-dimethoxyethane, bis(2-methoxyethyl)ether, dioxane or tetrahydrofuran. Tetrahydrofuran is preferably used.

The International Application PCT/EP 03/50873, describes a process to prepare cycloorganyl phosphanes of the formula $(R^1P)_n$ by reacting $R^1PHal_2$ with an alkali metal or an alkaline-earth metal in an organic solvent such as toluene in the presence of an activator, e.g. N,N,N',N'-tetramethylethylenediamine (TMEDA).

Furthermore, PCT/EP 03/50873 describes the preparation of sodium ceatena-oligophosphane-α,ω-diides, e.g. the preparation of $Na(L)_3[Na_5(P_2Ph_2)_3(L)]$ (L=solvent), which can react with mesitoylchloride (MesCO-Cl) to obtain acylphosphanes of the formula $PhP(COMes)_2$.

H. Schindlbauer et al (Monatshefte Chemie 90 148 [1959]) describes a method for producing phosphanes by reacting $R_1PHal_2$ with 4 equivalents of highly dispersed sodium in toluene to obtain $R^1PNa_2$ and subsequent reaction with alcohol/water. The alcohol used is ethanol.

The Schindibauer process has the drawback that a considerable amount of undesired by-products are obtained which need to be removed.

Accordingly, there still remains a need for a process to produce acylphosphanes directly from an organic phosphorus halide resulting in a high yield and a substantially complete conversion.

It has been found that the required selectivity can be achieved by using a proton source like sterically hindered alcohols, trialkylamine hydrohalogenes, bisarylamines, malono nitrile, malonic acid esters, amidine hydrohalogene and carboxylic acids.

The invention relates to a process for the preparation of acylphosphanes of formula I

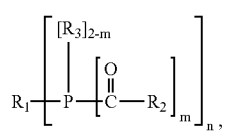

wherein
n and m are each independently of the other 1 or 2;
$R_1$, if n=1, is
$C_1$-$C_{18}$alkyl, $C_2$-$C_{18}$alkyl which is interrupted by one or several non-successive O atoms; phenyl-$C_1$-$C_4$alkyl, $C_2$-$C_8$alkenyl, phenyl, naphthyl, biphenyl, $C_5$-$C_{12}$cycloalkyl or a 5- or 6-membered O-, S- or N-containing heterocyclic ring, the radicals phenyl, naphthyl, bi-phenyl, $C_5$-$C_{12}$cycloalkyl or the 5- or 6-membered O-, S- or N-containing heterocyclic ring being unsubstituted or substituted by one to five halogen, $C_1$-$C_8$alkyl, $C_1$-$C_8$alkylthio, $C_1$-$C_8$alkoxy and/or —$N(R_8)_2$;
$R_1$, if n=2, is
$C_1$-$C_{18}$alkylene, $C_2$-$C_{18}$alkylene which is interrupted by one or several non-successive O atoms; or $R_1$ is $C_1$-$C_6$alkylene which is substituted by $C_1$-$C_4$alkoxy, phenyl, $C_1$-$C_4$alkyl-phenyl, phenyl-$C_1$-$C_4$alkyl or $C_1$-$C_6$alkoxyphenyl; or $R_1$ is phenylene or xylylene, which radicals are unsubstituted or substituted by one to three $C_1$-$C_4$alkyl and/or $C_1$-$C_4$alkoxy, or $R_1$ is a

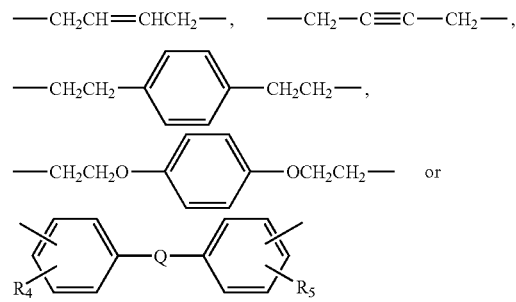

group;
$R_2$ is $C_1$-$C_{18}$alkyl, $C_3$-$C_{12}$cycloalkyl, $C_2$-$C_{18}$alkenyl, phenyl-$C_1$-$C_4$alkyl, phenyl, naphthyl, biphenyl or a 5- or 6-membered O-, S- or N-containing heterocyclic ring, the radicals phenyl, naphthyl, biphenyl or the 5- or 6-membered O-, S- or N-containing heterocyclic ring being unsubstituted or substituted by one to five halogen, $C_1$-$C_8$alkyl, $C_1$-$C_8$alkoxy and/or $C_1$-$C_8$alkylthio;
$R_3$ is $C_1$-$C_{18}$alkyl, $C_2$-$C_{18}$alkyl which is interrupted by one or several non-successive O atoms or which is interrupted by —CO—, —COO—, —OCO—, —OCOO—, —CO—N($R_9$), —N($R_9$)—CO—, —N($R_9$)—CO—N($R_9$)—, —N($R_9$)—COO—; $C_1$-$C_{18}$ alkyl substituted by —$OR_{10}$, —OCO—$R_{10}$, —COO—$R_{10}$, —N($R_9$)—CO—$R_{10}$, —CO—N($R_8$)—$R_{10}$, —C($R_{11}$)=C($R_{12}$)—CO—$OR_{10}$ or —C($R_{11}$)=C($R_{12}$)-phenyl; $C_2$-$C_{12}$alkenyl or $C_2$-$C_{12}$alkenyl which is interrupted by one or several non-successive O atoms; phenyl-$C_1$-$C_4$alkyl, phenyl, naphthyl, biphenyl, $C_5$-$C_{12}$cycloalkyl or a 5- or 6-membered O-, S- or N-containing heterocyclic ring, the radicals phenyl, naphthyl, biphenyl, $C_5$-$C_{12}$cycloalkyl or the 5- or 6-membered O-, S- or N-containing heterocyclic ring being unsubstituted or substituted by one to five halogen, $C_1$-$C_8$alkyl, $C_1$-$C_8$alkylthio $C_1$-$C_8$alkoxy and/or —$N(R_8)_2$; or $R_3$ is —CO—$OR_9$ or —CO—$N(R_9)_2$;
Q is a single bond, $CR_6R_7$, —O— or —S—;
$R_4$ and $R_5$ are each independently of the other hydrogen, $C_1$-$C_4$alkyl or $C_1$-$C_4$alkoxy;

$R_5$ and $R_7$ are each independently of the other hydrogen or $C_1$-$C_4$alkyl;

$R_8$ is $C_1$-$C_{18}$ alkyl, $C_2$-$C_{18}$ alkyl which is interrupted by one or several non-successive O-atoms; or —N($R_8$)$_2$ forms a 5- or 6-membered O-, S- or N-containing heterocyclic ring;

$R_9$ is hydrogen, $C_1$-$C_{18}$alkyl, $C_2$-$C_{18}$alkyl which is interrupted by one or several non-successive O atoms, $C_3$—$CO_{12}$-cycloalkyl, $C_1$-$C_{18}$-alkenyl, phenyl-$C_1$-$C_4$-alkyl, phenyl, naphthyl, pyridyl, the radicals phenyl, naphthyl or pyridyl being unsubstituted or substituted by one to five $C_1$-$C_8$-alkyl, $C_1$-$C_8$-alkoxy, $C_1$-$C_8$-alkylthio and/or halogen; or —N($R_9$)$_2$ forms a 5- or 6-membered O-, S- or N-containing heterocyclic ring;

$R_{10}$ is $C_1$-$C_{18}$alkyl, $C_2$-$C_{18}$alkyl which is interrupted by one or several non-successive O-atoms, $C_3$-$C_{12}$-cycloalkyl, phenyl-$C_1$-$C_4$-alkyl, $C_2$-$C_{18}$-alkenyl, phenyl, naphthyl, biphenyl;

the radicals phenyl-$C_1$-$C_4$-alkyl, phenyl, naphthyl or biphenyl being unsubstituted or substituted by one to five $C_1$-$C_8$-alkyl, $C_1$-$C_8$-alkoxy, $C_1$-$C_8$-alkylthio and/or halogen;

$R_{11}$ is hydrogen or $C_1$-$C_4$-alkyl;

$R_{12}$ is hydrogen or $C_1$-$C_4$-alkyl;

by (1) reacting a phosphorous halide of formula IIa or a phosphorous halide oxide of formula IIb or a phosphorous halide sulfide of formula IIc

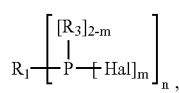
(IIa)

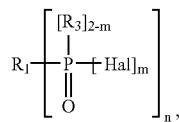
(IIb)

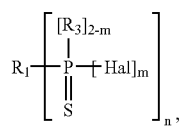
(IIc)

wherein $R_1$, $R_3$, n and m have the meaning cited above and Hal is F, Cl, Br or I;

with an alkali metal in a solvent in the presence of a proton source like sterically hindered alcohols, trialkylamine hydrohalogenes, bisarylamines, malono nitrile, malonic acid esters, amidine hydrohalogene and carboxylic acids;

(2) subsequent reaction with m acid halides of formula III

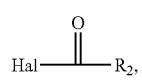
(III)

wherein $R_2$, Hal and m have the meaning cited above.

In another of its aspect, this invention relates to a process for the preparation of monoacylphosphanes of the formula I' (compounds of the formula I with n=1 and m=1)

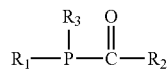
(I')

wherein $R_1$, $R_2$ and $R_3$ are as defined above, by (1) reacting organic phosphorus halides of formula II'

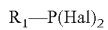
(II')

wherein $R_1$ and Hal are as defined above, with an alkali metal in a solvent in the presence of a proton source like sterically hindered alcohols, trialkylamine hydrohalogenes, bisarylamines, malono nitrile, malonic acid esters, amidine hydrohalogene and carboxylic acids;

(2) subsequent reaction with an acid halide of formula III'

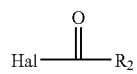
(III')

wherein $R_2$ and Hal are as defined above, followed by the reaction with an electrophilic compound $R_3$-Hal, wherein $R_3$ and Hal are as defined above, or vice versa.

The sequence of addition of the acid halide and the compound $R_3$-Hal can be interchanged. Thus, it is possible to add first the compound $R_3$-Hal and then the acid halide.

In another of its aspect, this invention relates to a process for the preparation of symmetric bisacylphosphanes of the formula I" (compounds of the formula I with n=1 and m=2)

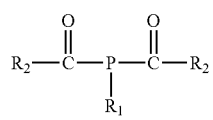
(I")

wherein $R_1$ and $R_2$ are as defined above by (1) reacting organic phosphorus halides of formula II"

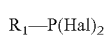
(II")

wherein $R_1$ and Hal are as defined above, with an alkali metal in a solvent in the presence of a proton source like sterically hindered alcohols, trialkylamine hydrohalogenes, bisarylamines, malono nitrile, malonic acid esters, amidine hydrohalogene and carboxylic acids;

(2) subsequent reaction with an acid halide of formula III"

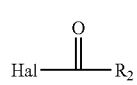
(III")

wherein $R_2$ and Hal are as defined above.

In another of its aspect, this invention relates to a process for the preparation of un-symmetric bisacylphosphanes of the formula I'" (compounds of the formula I with n=1 and m=2)

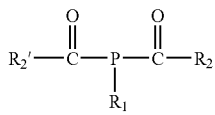
(I''')

wherein R₁ is as defined above and R₂ and R₂' independently of one another are as defined above under R₂ with the proviso that R₂ is not equal R₂'
by
(1) reacting organic phosphorus halides of formula II''

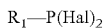  (II'')

wherein R₁ and Hal are as defined above,
with an alkali metal in a solvent in the presence of a proton source like sterically hindered alcohols, trialkylamine hydrohalogenes, bisarylamines, malono nitrile malonic acid esters, amidine hydrohalogene and carboxylic acids;
(2) subsequent reaction with an acid halide of formula III''

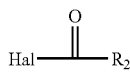
(III'')

wherein R₂ and Hal are as defined above,
(3) subsequent reaction with a second acid halide III'''

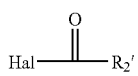
(III''')

wherein R₂' and Hal are as defined above.

In another of its aspects, this invention also relates to a process for the preparation of mono acylated phosphanes of the formula VI and VI'

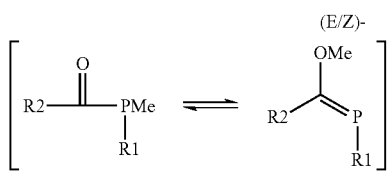
VI

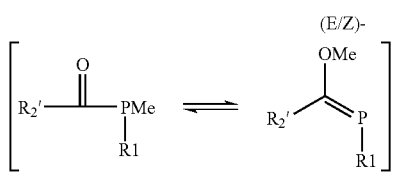
VI' where R₁, R₂, R₂' are defined as above and Me is Li, Na, K,
by
(1) reacting organic phosphorus halides of formula II''

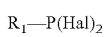 (II')

wherein R₁ and Hal are as defined above,
with an alkali metal in a solvent in the presence of a proton source like sterically hindered alcohols, trialkylamine hydrohalogenes, bisarylamines, malono nitrile, malonic acid esters, amidine hydrohalogene and carboxylic acids;
(2) subsequent reaction with an acid halide of formula III'' or III'''

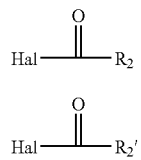
(III'')

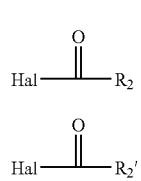
(III''')

wherein R₂, R₂' and Hal am as defined above.

The mono acylated phosphanes of formula VI and VI' can be isolated by standard techniques known to the person skilled in the art.

Compounds of formula VI and VI' can serve as starting materials for the synthesis of compounds of formula I', I'' and I''' as described above.

In another aspect of the invention step (1) is carried out by reacting diphospanes of the formula (R₁)₂—P—P(R₁)₂ or polyphosphanes of the formula [R₁P]ₙ, wherein R₁ is as defined above and n is ≧3, with an alkali metal in a solvent in the presence of a proton source like sterically hindered alcohols, trialkylamine hydrohalogenes, bisarylamines, malono nitrile, malonic acid esters, amidine hydrohalogene and carboxylic acids; followed by the reaction with acid halides (III, III', III'', III''') and/or by reaction with electrophilic compounds R₃-Hal.

In another of its aspects, this invention relates to a process for the preparation of acylphosphane oxides and acylphosphane sulfides of formula IV

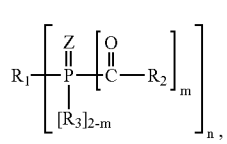
(IV)

wherein
R₁, R₂, R₃, n and m are as defined above, and Z is O or S, by oxidation or reaction with sulfur of the acylphosphane of formula I, I', I'' or I'''.

The proton source is selected from sterically hindered alcohols, trialkylamine hydro-halogenes, bisarylamines, malono nitrile, malonic acid esters, amidine hydrohalogene and carboxylic acids.

The sterically hindered alcohol is selected from the group consisting of secondary or tertiary $C_3$-$C_{18}$alcohols, preferably of t-butanol, tert.-amyl-alcohol, 3-methyl-3-pentanol, 3-ethyl-3-pentanol, triphenylmethanol, 3,7-dimethyl-3-octanol, 2-methyl-1-phenyl-2-propenol, 2-methyl-4-phenyl-2-butanol, fenchyl alcohol, 2,4-dimethyl-3-pentanol, 1-dimethylamino-2-propanol or hexylene glycol.

The trialkylamine hydrohalogene is selected from tert. ($C_1$-$C_8$)₃N—HCl, preferably trimethylamine hydrochloride, triethylamine hydrochloride or tributylamine hydrochloride.

Suitable alkali metals are lithium, sodium or potassium, preferably sodium. It is also possible to use magnesium in combination with lithium.

$C_1$-$C_{18}$Alkyl is linear or branched and is, for example, $C_1$-$C_{12}$-, $C_1$-$C_8$-, $C_1$-$C_5$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl or octadecyl.

$C_1$-$C_{12}$-, $C_1$-$C_5$- and $C_1$-$C_4$Alkyl are also linear or branched and have, for example, the meanings cited above up to the corresponding number of carbon atoms.

$C_2$-$C_{18}$Alkyl, which is interrupted once or several times by non-successive —O—, is interrupted, for example, 1-9, e.g. 1-7, 1-5, 1-3 or 1 or 2, times by —O—, the O atoms always being interrupted by at least one methylene group. The alkyl groups may be linear or branched. The structural units obtained are thus, for example, —CH$_2$—O—CH$_3$, —CH$_2$CH$_2$—O—CH$_2$CH$_3$, —[CH$_2$CH$_2$O]$_y$CH$_3$, where y=1-8, —(CH$_2$CH$_2$OCH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

$C_2$-$C_{18}$Alkenyl radicals may be mono- or polyunsaturated, linear or branched and are, for example, vinyl, allyl, methallyl, 1,1-dimethylallyl, propenyl, butenyl, pentadienyl, hexenyl or octenyl, preferably vinyl or allyl, $R_2$ defined as $C_2$-$C_{18}$alkenyl is typically $C_2$-$C_8$—, $C_2$-$C_8$—, preferably $C_2$-$C_4$alkenyl.

$C_5$-$C_{12}$Cycloalkyl is, for example, cyclopentyl, cyclohexyl, cyclooctyl, cyclododecyl, preferably cyclopentyl and cyclohexyl, more preferably cyclohexyl. $C_3$-$C_{12}$Cycloalkyl is additionally e.g. cyclopropyl.

$C_1$-$C_8$Alkoxy is linear or branched radicals and is typically methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy or octyloxy, preferably methoxy, ethoxy, propoxy, isopropoxy, n-butyloxy, sec-butyloxy, isobutyloxy, tert-butyloxy, most preferably methoxy.

Halogen is fluoro, chloro, bromo and iodo, preferably chloro and bromo, most preferably chloro.

Examples of O-, S- or N-containing 5- or 6-membered heterocyclic rings are furyl, thienyl, pyrrolyl, oxinyl, dioxinyl or pyridyl. The cited heterocyclic radicals may be substituted by one to five, e.g. by one or two, linear or branched $C_1$-$C_8$alkyl, halogen and/or $C_1$-$C_8$alkoxy. Examples of such compounds are dimethylpyridyl, dimethylpyrrolyl or methylfuryl.

Examples for —N(Ra$_8$)$_2$, —N(R$_9$)$_2$ forming a 5- or 6-membered O-, S- or N-containing heterocyclic rings are:

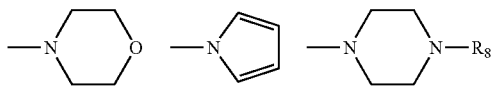

with $R_8$ as defined above.

Substituted phenyl, naphthyl or biphenyl is substituted by one to five, e.g. by one, two, three or four, preferably by one, two or three, for example linear or branched $C_1$-$C_8$alkyl, linear or branched $C_1$-$C_8$alkoxy or by halogen.

Preferred substituents for phenyl, naphthyl and biphenyl are $C_1$-$C_4$alkyl, preferably methyl, $C_1$-$C_4$alkoxy, more preferably methoxy, and chloro. Particularly preferred substituents are, for example, 2,4,6-trimethylphenyl, 2,6-dichlorophenyl, 2,6-dimethylphenyl or 2,6-dimethoxyphenyl.

$R_2$ is, for example, $C_1$-$C_{18}$alkyl or phenyl, preferably 2,4,6-trimethylphenyl, 2,6-dimethylphenyl or 2,6-dimethoxyphenyl, most preferably 2,4,6-trimethylphenyl.

$R_1$ and $R_3$ are preferably unsubstituted phenyl, $C_1$-$C_6$alkyl-substituted phenyl or $C_1$-$C_6$alkoxy-substituted phenyl, most preferably phenyl.

$R_1$ defined as $C_1$-$C_{18}$alkylene is linear or branched alkylene, such as methylene, ethylene, propylene, isopropylene, n-butylene, sec-butylene, isobutylene, tert-butylene, pentylene, hexylene, heptylene, octylene, nonylene, decylene, dodecylene, tetretadecylene, heptadecylene or octadecylene. $R_1$ is preferably $C_1$-$C_{12}$alkylene, e.g. ethylene, decylene,

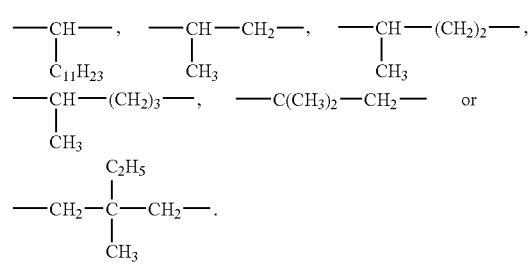

If $R_1$ is $C_2$-$C_{18}$alkylene which is interrupted by one or several non-successive O atoms, then structural units such as —CH$_2$—O—CH$_2$—, —CH$_2$CH$_2$—O—CH$_2$CH$_2$—, —[CH$_2$CH$_2$O]$_y$— are obtained, where y=1-9, —(CH$_2$CH$_2$O)$_7$ CH$_2$CH$_2$— or —CH$_2$—CH(CH$_3$—O—CH$_2$—CH(CH$_3$)—.

If alkylene is interrupted by several O atoms, then these O atoms are always separated from each other by at least one methylene group.

Phenyl-$C_1$-$C_4$alkyl is, for example, benzyl, phenylethyl, α-methylbenzyl or α,α-dimethyl-benzyl, preferably benzyl. Phenyl-$C_1$-$C_2$alkyl is particularly preferred.

$C_1$-$C_4$Alkylphenyl is typically tolyl, xylyl, mesityl, ethylphenyl, diethylphenyl, preferably tolyl or mesityl.

$C_1$-$C_6$Alkoxyphenyl is phenyl which is substituted by one to four alkoxy radicals, for example 2,6-dimethoxyphenyl, 2,4-dimethoxyphenyl, 2,4 dipentoxyphenyl, methoxyphenyl, ethoxyphenyl, propoxyphenyl or butoxyphenyl.

Phenylene is 1,4-, 1,2- or 1,3-phenylene, preferably 1,4-phenylene.

If phenylene is substituted, it is mono- to tetra-substituted, e.g. mono-, di- or trisubstituted, preferably mono- or disubstituted, at the phenyl ring. Xylylene is o-, m- or p-xylylene:

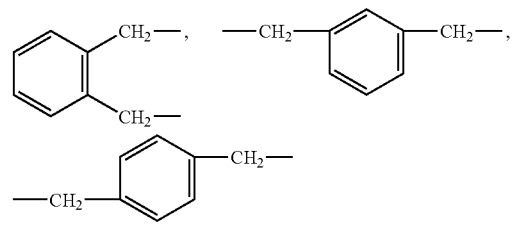

and is, for example, mono- to tetrasubstituted, e.g. mono-, di- or trisubstituted, preferably mono- or disubstituted, at the phenyl ring.

Preferred substituents:

In the above-described processes, $R_1$, if n=1, is $C_1$-$C_{12}$alkyl, cyclohexyl, phenyl or biphenyl, the radicals phenyl and biphenyl being unsubstituted or substituted by one to four $C_1$-$C_8$alkyl and/or $C_1$-$C_8$alkoxy;

$R_1$, if n=2, is $C_6$-$C_{10}$alkylene, or

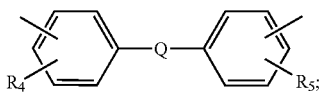

$R_3$ is $C_1$-$C_{12}$alkyl, cyclohexyl, phenyl or biphenyl, the radicals phenyl and biphenyl being un-substituted or substituted by one to four $C_1$-$C_8$alkyl and/or $C_1$-$C_8$alkoxy;

Q is a single bond or —O—, and $R_4$ and $R_5$ are hydrogen.

Compounds to be highlighted in the above processes are those of formula I, wherein $R_2$ is phenyl which is substituted in 2,6- or 2,4,6-position by $C_1$-$C_4$alkyl and/or $C_1$-$C_4$alkoxy.

Compounds of formula I which are particularly preferably used in the above process are those wherein n is 1.

The residue "Hal" is preferably chloro.

Other preferred compounds of formula I in the above process are those, wherein m is defined as the number two, i.e. bisacylphosphane or bisacylphosphane oxides or bisacylphosphane sulfides.

A preferred process is that, wherein in formula, I, n is 1, m is 1 or 2, $R_1$ is phenyl which is un-substituted or substituted by $C_1$-$C_4$alkyl or $C_1$-$C_8$alkoxy, or $R_1$ is $C_1$-$C_{12}$alkyl; $R_2$ is $C_1$-$C_{18}$alkyl or phenyl which is substituted by halogen, $C_1$-$C_4$alkoxy or $C_1$-$C_4$alkyl; and $R_3$ is unsubstituted or $C_1$-$C_4$alkyl-substituted phenyl.

In the novel process for the preparation of mono- and bisacylphosphanes, an organic phosphorous halide of formula IIa or a phosphorous halide oxide of formula IIb or a phosphorous halide sulfide of formula IIc is first reacted in a solvent with an alkali metal in the presence of a proton source like sterically hindered alcohols, trialkylamine hydrohalogenes, bisarylamines, malono nitrile, malonic acid esters, amidine hydrohalogene and carboxylic acids.

This first step includes two different reaction types, a metallation and a reduction step.

The metallation is carried out by reacting a compound of the formula IIa, IIb, or IIc with an alkali metal in a solvent, whereby a metallized phosphanide of the formula V $$R_1—P(Me)-P(Me)-R_1 \quad (V)$$

is formed together with cyclic phosphanes $(R_1P)_n$, n≧3 as intermediates. Me is lithium, sodium or potassium or magnesium in combination with lithium and $R_1$ is as defined above.

It is useful to employ from 4 to 6 atom equivalents of an alkali metal in solid or molten form, preferably sodium, for the preparation of bisacylphosphanes or monoacylphosphanes prepared from $R_1PHal_2$, and 2 to 3 atom equivalents of an alkali metal in solid or molten form for the preparation of monoacylphosphanes prepared from $(R_1)_2PHal$. It is not necessary that the alkali metal is highly dispersed.

Catalytic amounts of alkali or earth alkali hydroxides or of Na, K or Li alcoholates or of alcohols, preferably sterically hindered alcohols may be added prior or during the metallation step.

In addition combinations of catalytic amounts of alkali and/or earth alkali metals and/or sterically hindered alcohols may be added prior or during the metallation step.

Catalytic amounts refer to ranges from 0.1-50 mol % with respect to the phosphorous organic compound IIa, IIb or IIc.

The reaction is carried out in an arene solvent such as in benzene, toluene, o-, m- or p-xylene, mesitylene, ethylbenzene, diphenylethane, 1,2,3,4tetrahydronaphtaline (tetraline), isopropylbenzene (cumol) or in mixtures thereof.

The reaction temperature is preferably above the melting temperature of sodium. It is recommended to stirr the reaction mixture.

The reduction is carried out by reacting the intermediate V and/or $(R_1P)_n$, n≦3 with a proton source like sterically hindered alcohols, trialkylamine hydrohalogenes, bisarylamines, malono nitrile, malonic acid esters, amidine hydrohalogene and carboxylic acids in the presence of surplus alkali metal from the metallation step whereby a protonated and/or a metallized phosphane (IId) and a protonated and/or metallized diphosphane (IIe) $R_1$—P(H,Me)-P(H,Me)-$R_1$ is formed via different intermediary steps as the main component.

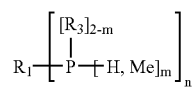

$R_1$, $R_3$, Me, m and n have the meaning cited above,

The amount of the diphosphane (IIe) can be influenced by appropriate addition of the above mentioned catalysts prior, during or after the metallation step. Preferred catalysts are, for example, alkali-or earth alkali hydroxides in amounts of 0.1-10 mol % with respect to the phosphorous organic compound IIa, IIb and IIc. Other preferred catalysts are, for example, Li, Na or K alcoholates, preferably alcoholates of sterically hindered alcohols and most preferably KOH and sterically hindered K-alcoholates in amounts of 5-50 mol % with respect to IIa, IIb and IIc.

In a further embodiment, the process starts with a birch-like reduction of diphospanes of the formula $(R_1)_2$—P—P$(R_1)_2$ or polyphosphanes of the formula $[R_1P]_n$, wherein $R_1$ is as defined above and n is ≧3 with a metal, preferably sodium, in the presence a proton source like sterically hindered alcohols, trialkylamine hydrohalogenes, bisarylamines, malono nitrile, malonic acid esters, amidine hydrohalogene and carboxylic acids to obtain phosphanes of the formula $R_1PH_2$ or $(R_1)_2PH$. The phosphanes are then reacted with an acid halide or an electrophilic compound $R_3$-Hal.

The above diphospanes of the formula $(R_1)_2$—P—P$(R_1)_2$ or polyphosphanes of the formula $[R_1P]_n$ may be prepared as describes in the Int. Application PCT/EP 03150873 by reacting $R_1PHal_2$ with an alkali metal or an alkaline-earth metal in an organic solvent such as e.g. in toluene optionally in the presence of an activator such as e.g. N,N,N',N'-tetramethylethylenediamine (TMEDA) or by reacting $R_1PHal_2$ with active zinc in the presence of a solvent.

The reduction step is the essential feature in the above-described novel process, as this step was shown to be largely responsible for the improved selectivity of the whole process.

The reduction step can be carried out in the presence of an activator such as amines (triethylamine, tributylamine, piperidine, morpholine, N-methylpiperidine, N-methyl morpholine) or polyamines such as, for example TMEDA=N,N,N', N'-tetramethylethylenediamine.

It is useful to employ from 1 to 2 equivalents of a proton source like sterically hindered alcohols, trialkylamine hydrohalogenes, bisarylamines, malono nitrile, malonic acid esters, amidine hydrohalogene and carboxylic acids. The solvent is preferably the same as in the metallation step.

The reaction temperatures are preferably in the range from −20° C. to +160° C., e.g. from 80° C. to 140° C.

The protonated and/or metallized phosphane (IId) and (IIe) obtained as described above is reacted in the next reaction step with acid halides (III, III', III", III''') or with electrophilic compounds R$_3$-Hal to the mono- or bisacylphosphane (I, I', I", I''').

In addition, it is also possible to directly react the metallized phosphanide (V) or the mixture of (V) with the cyclic phosphanes (R$_1$P)$_n$, n>=3, with the acid halides (III, III', III", III''') or with electrophilic compounds R$_3$-Hal to the mono- or bisacylphosphane (I, I', I", I''').

The solvents used may be, for example, the same as those used above for the first step. However, it is also possible to remove the solvent used in the first step by distillation and to take up the residue in another solvent and then to further process it. It is preferred to work in the same solvent as in the preceding step, preferably in xylene or toluene.

It is possible to add polar or dipolar co-solvents to the reaction mixture during or after the reduction step. Such solvents may be linear or cyclic amides like dimethylacetamide (DMA), n-methyl pyrrolidone (NMP), cydic ureas like 1,3-dimethypropylene urea (DMPU), linear and cyclic glycols like diglyme and dimethoxyethane (DME).

The reaction temperatures for the reaction with the acid halide are usefully in the range from −20° to +80° C.

The mono- or bisacylphosphane of formula I can be isolated by the customary technological methods which are known to the skilled person, for example by filtration, evaporation or distillation. Likewise, the customary methods of purification may be used, for example crystallisation, distillation or chromatography.

However, the phosphanes can also be reacted without isolation to the corresponding mono- or bisacylphosphane oxides or mono- or bisacylphosphane sulfides.

Using the process of this invention it is also possible to prepare mono- and bisacylphosphanes together in one reaction step.

Depending on the substituents used, unsymmetric compounds may be formed by the novel process.

Monoacylphosphane oxides are compounds of the formula I' corresponding to compounds of the formula I wherein n=1 and m=1.

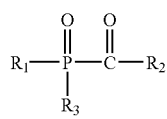

(I')

The residues R$_1$ and R$_3$ may be the same or may be different.

Bisacylphosphane oxides are compounds of the formula I''' corresponding to compounds of the formula I wherein n=1 and m=2.

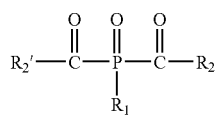

(I''')

The residues R$_2$ and R$_2$' may be the same or may be different.

By means of the novel process it is furthermore also possible to prepare mixtures of aliphatic and aromatic monoacylphosphanes or mixtures of aliphatic and aromatic bisacylphosphanes.

If required, all of the mixtures may be separated by the processes customarily used in the technology or they may be further used as they are.

This invention also relates to a process for the preparation of mono- and bisacylphosphane oxides or mono- and bisacylphosphane sulfides. This process is first carried out as described above and a mono- or bisacylphosphane (I) is prepared. The crude reaction product (I) can then be further processed without purification and an additional reaction step may be carried out without isolation of the phosphane (I) using the solution of the crude product. If required, the solvent may be changed, for example, by concentrating the solution containing the mono- or bisacylphosphane and taking up the residue in a new solvent. Of course it is also possible to further react above-described unseparated mixtures of compounds of formula (I) to the corresponding oxide or sulfide.

It is recommended to adjust the p$_H$ of the reaction mixture prior to the oxidation step to a p$_H$ of 2-8, preferabyl to a p$_H$ of 3-6 by addition of typical inorganic and/or organic acids or buffer systems.

When preparing the respective oxide (IVa), the oxidation of the phosphane (I) is carried out using the oxidant conventionally used in the technology:

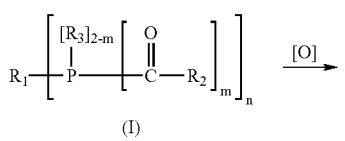

(I)

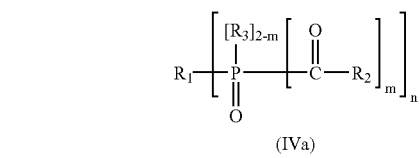

(IVa)

Suitable oxidants are in particular hydrogen peroxide and organic peroxy compounds, for example peracetic acid or t-butylhydroperoxide, air or pure oxygen.

The oxidation is usefully carried out in solution. Suitable solvents are aromatic hydrocarbons, such as benzene, toluene, m-xylene, p-xylene, ethylbenzene or mesitylene, or aliphatic hydrocarbons, such as alkanes and alkane mixtures, e.g. petroleum ether, hexane or cyclohexane. During oxidation, the reaction temperature is preferably kept in the range from 0° to 120° C., preferably from 200 and 80° C.

The reaction products (IVa) can be isolated and purified by conventional processing methods known to the skilled person.

The respective sulfide (IVb) is prepared by reaction with sulfur:

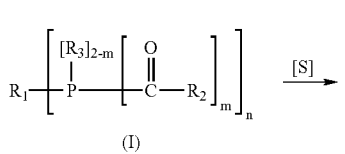

(I)

-continued

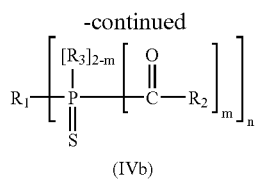

(IVb)

The mono- or bisacylphosphanes (I) are in this case reacted in substance or, where appropriate, in a suitable inert organic solvent with an equimolar to 2-fold molar amount of elementary sulfur. Suitable solvents are for example those described for the oxidation reaction. However, it is also possible to use e.g. aliphatic or aromatic ethers, such as dibutyl ether, dioxane, diethylene glycol dimethyl ether or diphenyl ether, in the temperature range from 200 to 250° C., preferably from 600 to 120° C. The resulting mono- or bisacylphosphane sulfide, or its solution, is usefully freed from any remaining elementary sulfur by filtration. After the solvent is removed, the mono- or bisacylphosphane sulfide can be isolated by distillation, chromatography or recrystallisation in pure form.

As mentioned above, it is also possible to use mixtures of compounds of formula I for the oxidation or reaction to the sulfide. The correspondingly obtained oxide or sulfide mixtures can either be separated by processes customarily used in the technology or may be used as mixtures.

All of the above reactions are usefully carried out with exclusion of air in an inert gas atmosphere, e.g. under nitrogen or argon gas. The respective reaction mixture is usefully also stirred.

The acid halides (III, III', III'', III''') or the electrophilic compounds $R_3$-Hal used as starting materials are known substances, some of which are commercially available, or may be prepared in analogy to known compounds.

The preparation of the phosphorus halides (II) is also described in a great number of publications and can be carried out in analogy to the descriptions provided there. In J. Chem. Soc. (1935), 462 and J. Chem. Soc. (1944), 276, W. Davies discloses for example the preparation of aryl phosphorus chlorides by reaction of arylene with phosphorus trichloride in the presence of aluminum trichloride. According to F. Nief, Tetrahedron 47 (1991) 33, 667 or Th. Knapp, Tetrahedron 40(1984) 4, 76, the Grignard reaction of aryl halides with magnesium and phosphorus trichloride is another possibility. According to S. Metzger, J. Org. Chem. 29 (1964), 627, alkylphosphorus chlorides are accessible in the same manner. In Helv. Chim. Act. 36 (1953), 1314, Th. Weil describes the reaction of aryl halides or alkyl halides with magnesium followed by the reaction with zinc chloride and subsequent reaction with phosphorus trichloride. The reaction of aryl halides with butyl lithium and phosphorus trichloride to the corresponding aryl phosphorus chloride is disclosed by G. Whitesides in JACS 96 (1974), 5398. According to Th. Knapp, Tetrahedron 40 (1984) 4, 765, the reaction of the aryl magnesium halide with bis(dimethylamino)phosphorus chloride followed by the reaction with hydrochloric acid also results in the desired starting material. According to A. Burg, U.S. Pat. No. 2,934,564, the same method may also be used for the preparation of the corresponding alkyl phosphorus chlorides.

It is characteristic of the novel process that the individual processing steps can be carried out directly one after the other without the need for isolating and purifying the respective intermediates.

Mixtures such as those described in the process for the preparation of the corresponding phosphanes may also be formed, or may also be specifically produced, in the above-described process for the preparation of mono- or bisacylphosphane oxides or mono- or bis-acylphosphane sulfides. Such mixtures can be separated by methods known in the technology or may be further used in the form of mixtures.

The phosphanes which are accessible by the novel process are important educts for the preparation of the corresponding phosphane oxides and phosphane sulfides. The phosphane oxides and phosphane sulfides are used in the art as initiators in photopolymerisation reactions.

The following examples illustrate the invention in more detail, although it is not intended that the invention be limited to the examples. As in the remaining description and in the patent claims, parts or percentages are by weight, unless otherwise stated.

EXAMPLES

General Solvents are used as received (without any treatment) or dried over molecular sieves or by azeotropic distillation. The course of the reaction is monitored by $^{31}$P-NMR spectroscopy.

Example 1

Basic Procedure for Experiments Collected in Tables 1-8 Preparation of bis(2,4,6-timethylbenzoyl)phenylphosphine oxide Using tert-butanol as Proton Source

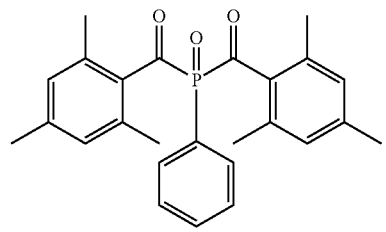

formula I''', $R_1$=phenyl, $R_2$, $R_2'$=mesityl;

a) Metallation of P,P-dichlorophenylphosphine in Toluene at 98-110° C.

Excluding moisture by an argon atmosphere, sodium lumps (20.61 g, 0.896 mol) are suspended at room temperature in toluene (870 g). This mixture is heated up to reflux with vigorous stirring starting as soon as the temperature reaches 98° C. After formation of a fine sodium suspension P,P-dichlorophenylphosphine (40.10 g, 0.224 mol) is dropwise added over one hour under vigorous stirring. Heating under reflux for an additional 16 h leads to the formation of a yellow precipitate.

b) Protonation/Reduction

The yellow suspension is dropwise treated with tert-butanol (33.20 g, 0.448 mol) over one hour at 98-110° C. Stirring is continued under reflux until all sodium is used up (ca. one hour).

c) Acylation

To the resulting thin, yellow suspension is added 2,4,6-trimethylbenzoyl chloride (82.12 g, 0.450 mol) at such a rate that the temperature is kept at 35-37° C. The mixture is then stirred for another hour at 35-37° C.

d) Oxidation using 30% $H_2O_2$ at 40-50° C.

To the resulting thin, light yellow suspension is dropwise added 30% hydrogen peroxide (76.16 g, 0.672 mol) at such a rate that the temperature is kept between 40-50° C. Stirring is continued for 2 h at 40-50° C. The light yellow suspension is treated with 250 g of 5% aqueous $NaHCO_3$, and then stirred for 5 min at 40-50° C. The two phases are separated and the organic phase washed with water (2×250 g). After evaporation of toluene, heptane (150 g) is added, the mixture heated up to 80° C. and then cooled to room temperature. The resulting solid is collected and washed with heptane (2×60 g). 71.0 g (75.7%) of bis(2,4,6-trimethylbenzoyl)phenylphosphine oxide are obtained as light yellow powder with a melting point of 130-131° C.

In the following tables conditions and results of typical experiments are summarized which have been conducted based on the procedure described in Example 1. Variations of conditions in synthetic steps indicated in the header of each table are related to the four steps a)-d) described in Example 1.

Abbreviations Conc.: concentration [mol $PhPCl_2$/total weight (in kg) of metallation reaction]; TMBCl=1,3,5-trimethylbenzoyl chloride; Equivalents (eq.) of reagents (Na, etc.) are related to the amount of $PhPCl_2$ (mol) used.

General Yields of bis(2,4,6-trimethylbenzoyl)-phenylphosphine oxide given in Table 2-8 have been calculated from the $^1$H-NMR spectra of the crude isolated product material. In some cases yields have been further confirmed by the isolation of pure bis(2,4,6-trimethylbenzoyl)-phenylphosphine oxide product via recrystallization from heptane or flash chromatography.

TABLE 1

Variation of conditions in the metallation step [see Example 1, a): reaction of $PhPCl_2$ with sodium metal]. No alcohol used.

| | | Metallation Step | | | |
|---|---|---|---|---|---|
| Entry | Solvent | Na [eq.] | Additive [eq.] | Temp [° C.] | Time [h] |
| 1 | Xylene | 4.0 | — | 140 | 1 |
| 2 | DEGDEE[a] | 4.0 | — | 20-100 | 3.5 |
| 3 | Toluene | 4.0 | TMEDA (0.5)[b] | 109 | 4 |
| 4 | Xylene | 4.0 | TMEDA (0.5) | 140 | 4 |
| 5 | Toluene | 4.0 | TMEDA (0.75) | 109 | 3 |
| 6 | Toluene | 4.0 | TMEDA (1.0) | 115 | 3 |
| 7 | Xylene | 3.0 | TMEDA (1.0) | 140 | 4 |
| 8 | Xylene | 4.0 | TMEDA (1.0) | 130 | 6 |
| 9 | Xylene | 4.0 | TMEDA (0.5) Naphthalene (0.1) | 25 | 2 |
| 10 | Xylene | 4.0 | DEGDEE (0.5)[b] | 140 | 4.5 |
| 11 | Xylene | 4.0 | Tributylamine (1.0) | 140 | 3.5 |
| 12 | Xylene | 4.0 | Piperidine (1.0) | 135 | 1 |
| 13 | Xylene | 4.0 | Piperidine (0.1) | 135 | 5 |
| 14 | Xylene | 3.0 | CuCl (0.1) | 110 | 19 |
| 15 | Toluene | — | Zinc (1.0) NaOH (1.0) | 20-45 | 3 |

[a]DEGDEE = diethylene glycol diethylether.
[b]TMEDA = N,N,N',N'-tetramethylethylenediamine.

TABLE 2

Variation of conditions in the metallation step (reaction of $PhPCl_2$ with sodium metal); Alcohol used: tert-butanol (1).

| | | Metallation Step | | | | | | |
|---|---|---|---|---|---|---|---|---|
| Entry | Solvent | Conc. [mol/kg] | Na [eq.] | Additive[a] [eq.] | Temp [° C.] | Alcohol [eq.] | TMBCl [eq.] | Yield [%] |
| 16 | Toluene | 0.2 | 4.0 | — | 98-110 | 2.0 | 2.0 | 76[c] |
| 17 | Toluene | 0.2 | 4.0 | TMEDA (1.2)[b] | 98-110 | 2.0 | 2.0 | 75[c] |
| 18 | Toluene | 0.2 | 4.0 | NaOH (0.05) | 98-110 | 2.0 | 2.0 | 71 |
| 19 | Toluene | 0.2 | 4.15 | — | 98-110 | 2.0 | 2.0 | 79[c] |
| 20 | Toluene | 0.2 | 4.15 | — | 98-110 | 2.3 | 2.15 | 92 |
| 21 | Toluene | 0.2 | 4.3 | — | 98-110 | 2.0 | 2.0 | 71 |
| 22 | Toluene | 0.2 | 4.8 | — | 98-110 | 2.0 | 2.35 | 54 |
| 23 | Toluene | 0.2 | 5.0 | — | 98-110 | 2.0 | 1.7 | 30 |
| 24 | Xylene | 0.2 | 4.0 | — | 130 | 2.0 | 2.0 | 71 |
| 25 | Xylene | 0.2 | 4.0 | $Na_2O_2$ (0.13) | 98-110 | 2.0 | 2.0 | 71 |
| 26 | Xylene | 0.2 | 4.4 | — | 120 | 2.4 | 2.0 | 76 |
| 27 | Toluene | 0.35 | 4.0 | — | 98-110 | 2.0 | 2.0 | 60[c] |
| 28 | Toluene | 0.4 | 4.0 | LiOtBu (0.15) | 98-110 | 2.0 | 2.0 | 78[d] |
| 29 | Toluene | 0.4 | 4.15 | — | 98-110 | 2.15 | 2.0 | 80 |
| 30 | Toluene | 0.4 | 4.15 | — | 98-110 | 2.3 | 2.15 | 83 |
| 31 | Xylene | 0.4 | 4.15 | — | 120-130 | 2.15 | 2.0 | 68 |
| 32 | Xylene | 0.4 | 4.15 | — | 120 | 2.3 | 2.15 | 81 |
| 33 | Ethylbenzene | 0.4 | 4.15 | — | 110-115 | 2.15 | 2.0 | 72 |
| 34 | Toluene | 0.4 | 4.15 | 1 (0.15) | 98-110 | 2.0 | 2.0 | 77 |
| 35 | Toluene | 0.4 | 4.15 | 1 (0.15) | 98-110 | 2.0 | 2.3 | 77 |
| 36 | Toluene | 0.4 | 4.15 | 1 (0.15) | 98-110 | 2.0 | 2.0 | 83[d] |
| 37 | Toluene | 0.4 | 4.15 | NaOH (0.04) | 98-110 | 2.0 | 2.0 | 79[c] |
| 38 | Toluene | 0.4 | 4.2 | NaOH (0.01) | 98-110 | 2.0 | 2.0 | 78[d] |
| 40 | Toluene | 0.4[e] | 4.2 | NaOH (0.01) | 98-110 | 2.0 | 1.9 | 70 |

[a]Additive is added to the reaction mixture prior to the metallation step.
[b]TMEDA = N,N,N',N'-tetramethylethylenediamine.
[c]Yield of pure bis(2,4,6-trimethylbenzoyl)phenylphosphine oxide after recrystallization from heptane; melting point 130-131° C.
[d]Prior to the oxidation reaction the pH has been adjusted to four.
[e]Liquid sodium.

TABLE 3

Variation of conditions in the metallation step (reaction of PhPCl$_2$ with sodium metal); Alcohol used: 3-methyl-3-pentanol (2).

| Entry | Solvent | Metallation Step Conc. [mol/kg] | Na [eq.] | Additive[a] [eq.] | Temp [°C.] | Alcohol [eq.] | TMBCl [eq.] | Yield [%] |
|---|---|---|---|---|---|---|---|---|
| 41 | Toluene | 0.24 | 4.15 | — | 98-110 | 2.0 | 2.0 | 75 |
| 42 | Toluene | 0.4 | 4.15 | — | 98-110 | 2.15 | 2.0 | 75 |
| 43 | Toluene | 0.4 | 4.15 | — | 98-110 | 2.15 | 2.15 | 80 |
| 44 | Toluene | 0.4 | 5.0 | — | 98-110 | 3.0 | 2.15 | 21 |
| 45 | Toluene | 0.4 | 4.5 | — | 98-110 | 2.1 | 2.15 | 64 |
| 46 | Toluene | 0.4 | 4.3 | — | 98-110 | 2.0 | 2.5 | 79 |
| 47 | Toluene | 0.4 | 4.05 | — | 98-110 | 2.1 | 2.2 | 76[b] |
| 48 | Toluene | 0.4 | 4.15 | 2 (0.15) | 98-110 | 2.0 | 2.2 | 78[b] |
| 49 | Toluene | 0.4 | 4.1 | DME (1.0) | 98-110 | 2.1 | 2.0 | 84 |
| 50 | Toluene | 0.4 | 4.0 | KOtBu (0.15) | 98-110 | 2.0 | 2.0 | 85[b] |
| 51 | Xylene | 0.4 | 4.15 | — | 98-110 | 2.15 | 2.15 | 80 |
| 52 | Xylene | 0.4 | 4.3 | — | 120-130 | 2.3 | 2.0 | 48 |
| 53 | Toluene | 0.45 | 4.15 | — | 98-110 | 2.0 | 2.0 | 66 |
| 54 | Toluene | 0.45 | 4.2 | — | 98-110 | 2.0 | 2.0 | 77 |
| 55 | Toluene | 0.7 | 4.1 | — | 98-110 | 2.1 | 2.1 | 74[b] |
| 56 | Toluene | 0.7 | 4.1 | — | 98-110 | 2.1 | 2.1 | 83[b)c] |
| 57 | Toluene | 0.7 | 4.2 | — | 98-110 | 2.0 (at 90° C.) | 2.0 | 55 |
| 58 | Toluene | 0.7 | 4.2 | — | 98-110 | 2.0 (at 90° C.) | 2.0 (at 90° C.) | 63 |
| 59 | Toluene | 0.7 | 4.2 | — | 98-110 | 2.2 (at 5° C.) | 2.0 | 75 |
| 60 | Toluene | 0.7 | 4.4 | — | 98-110 | 2.4 | 2.5 (at 5° C.) | 82 |
| 61 | Toluene | 0.7 | 4 | 2 (0.01) | 98-110 | 2.0 | 2.0 | 72 |
| 62 | Toluene | 0.7 | 4.1 | 2 (0.01) | 98-110 | 2.09 | 2.0 | 78 |
| 63 | Toluene | 0.7 | 4.2 | 2 (0.01) | 98-110 | 2.0 | 2.35; KOtBu (0.22) | 76 |
| 64 | Toluene | 0.7 | 4.0 | KOtBu (0.05) | 98-110 | 2.0 | 2.0 | 70 |
| 65 | Toluene | 0.7 | 4.1 | KOtBu (0.05) | 98-110 | 2.1 | 2.0 | —[i] |
| 66 | Toluene | 0.7 | 4.0 | KOtBu (0.1) | 98-110 | 2.0 | 2.0 | 88[d] |
| 67 | Toluene | 0.7 | 4.0 | KOtBu (0.1) | 98-110 | 2.0 | 2.0 | 89[c)g] |
| 68 | Toluene | 0.7 | 4.0 | KOtBu (0.1) | 98-110 | 2.0[e] | 2.0 | 86 |
| 69 | Toluene | 0.7 | 4.0 | KOtBu (0.1) | 98-110 | 2.0[f] | 2.0 | 88 |
| 70 | Toluene | 0.7 | 4.05 | KOtBu (0.1) | 98-110 | 2.0 | 1.74 | 70 |
| 71 | Toluene | 0.7 | 4.1 | KOtBu (0.1) | 98-110 | 2.0 | 2.1 | 74 |
| 72 | Toluene | 0.7 | 4.15 | KOtBu (0.1) | 98-110 | 2.0 | 2.2 | 74 |
| 73 | Toluene | 0.7 | 4.0 | KOtBu (0.1) | 98-110 | 2.0; KOtBu (0.05) | 2.0 | —[i] |
| 74 | Toluene | 0.7 | 4.0 | KOtBu (0.1) | 98-110 | 2.0 | 2.0; KOtBu (0.1) | 76 |
| 75 | Toluene | 0.7 | 4.0 | KOtBu (0.15) | 98-110 | 2.0 | 2.0 | —[i] |
| 76 | Toluene | 0.7 | 4.0 | KOtBu (0.20) | 98-110 | 2.0 | 2.0 | —[i] |
| 77 | Toluene | 0.7 | 4.0 | KOH (0.1) | 98-110 | 2.0 | 2.0 | —[i] |
| 78 | Toluene | 0.7 | 4.0 | KOH (0.1) 2 (0.1) | 98-110 | 2.0 | 2.0 | 81[h] |
| 79 | Toluene | 0.7 | 4.0 | KCl (0.1) | 98-110 | 2.0 | 2.0 | —[i] |
| 80 | Toluene | 0.7 | 4.0 | KOAc (0.1) | 98-110 | 2.0 | 2.0 | —[i] |
| 81 | Toluene | 0.79 | 4.2 | — | 98-110 | 2.0 | 2.0 | 70 |
| 82 | Toluene | 0.9 | 4.2 | 2 (0.02) | 98-110 | 2.0 | 2.0 | 72[h] |
| 83 | Toluene | 0.9 | 4.2 | 2 (0.01) | 98-110 | 2.2 | 2.2 | 68 |
| 84 | Toluene | 0.9 | 4.2 | NaOtBu (0.02) | 98-110 | 2.2 | 2.0 | 69 |
| 85 | Toluene | 1.0 | 4.0 | KOtBu (0.1) | 98-110 | 2.0 | 2.0 | 75 |

[a]Additive is added to the reaction mixture prior to the metallation step.
[b]Prior to the oxidation reaction the pH has been adjusted to four.
[c]The oxidation has been performed with 1.5 equiv. of peracetic acid solution instead of aqueous 30% hydrogen peroxide.
[d]80% yield of pure bis(2,4,6-trimethylbenzoyl)phenylphosphine oxide has been obtained after recrystallization from heptane.
[e]3-Methyl-3-pentanol has been distilled off under vacuum during the acylation reaction (ca. 25% of the total amount of 3-methyl-3-pentanol used).
[f]3-Methyl-3-pentanol has been distilled off under vacuum during the acylation reaction (ca. 50% of the total amount of 3-methyl-3-pentanol used).
[g]82% yield of pure bis(2,4,6-trimethylbenzoyl)phenylphosphine oxide has been obtained after recrystallization from heptane.
[h]Yield of pure bis(2,4,6-trimethylbenzoyl)phenylphosphine oxide after recrystallization from heptane.
[i]Yield not determined.

TABLE 4

Variation of proton source (alcohol etc.) in the protonation/reduction step.

| Entry | Solvent | Conc. [mol/kg] | Na [eq.] | Protonation/Reduction Step Proton Source [eq.] | TMBCl [eq.] | Yield [%] |
|---|---|---|---|---|---|---|
| 86 | Toluene | 0.24 | 4.5 | Ethanol (2.0) | — | — |
| 87 | Toluene | 0.27 | 4.0 | Isopropanol (2.0) | 2.0 | <50 |
| 88 | Xylene | 0.2 | 4.0 | tert-Butanol (2.0) | 2.0 | 66 |
| 89 | Xylene | 0.2 | 4.15 | tert-Butanol (2.0) | 2.0 | 81 |
| 90 | Toluene | 0.4 | 4.15 | tert-Butanol (2.0) | 2.0 | 75 |
| 91 | Toluene | 0.4 | 4.15 | tert-Butanol (2.3) | 2.15 | 83 |
| 92 | Xylene | 0.4 | 4.15 | tert-Butanol (2.3) | 2.15 | 81 |
| 93 | Xylene | 0.2 | 4.0 | 2-Methyl-2-butanol (2.0) | 2.0 | 69 |
| 94 | Xylene | 0.2 | 4.0 | 3-Methyl-3-pentanol (2.0) | 2.0 | 74 |
| 95 | Xylene | 0.4 | 4.15 | 3-Methyl-3-pentanol (2.15) | 2.15 | 79 |
| 96 | Toluene | 0.4 | 4.15 | 3-Methyl-3-pentanol (2.15) | 2.15 | 80 |
| 97 | Xylene | 0.2 | 4.0 | Triphenylmethanol (2.0)[a] | 2.0 | 50 |
| 98 | Xylene | 0.2 | 4.0 | Acetic acid (3.0)[b] | 3.0 | 14 |
| 99 | Toluene | 0.2 | 4.5 | Tributylamine hydrochloride (2.07) | 2.0 | 45 |
| 100 | Xylene | 0.2 | 4.0 | 2-Methyl-4-phenyl-2-butanol (2.0) | 2.0 | 59 |
| 101 | Xylene | 0.2 | 4.0 | 1-Dimethylamino-2-propanol (2.0) | 2.0 | <50 |
| 102 | Xylene | 0.2 | 4.0 | Hexylene glycol (2.0) | 2.0 | <50 |
| 102 | Xylene | 0.2 | 4.0 | 2-Methyl-1-phenyl-2-propanol (2.0) | 2.0 | 62 |
| 103 | Toluene | 0.2 | 4.15 | 2-Methyl-1-phenyl-2-propanol (2.0) | 2.0 | 69 |
| 104 | Toluene | 0.2 | 4.15 | 1R-endo-(+)-Fenchyl alcohol (2.0) | 2.0 | 68 |
| 105 | Toluene | 0.2 | 4.15 | 2,4-Dimethyl-3-pentanol (2.0) | 2.0 | 71 |
| 106 | Toluene | 0.2 | 4.15 | 3,7-Dimethyl-3-octanol (2.15) | 2.15 | 76 |
| 107 | Toluene | 0.2 | 4.15 | 3-Ethyl-3-pentanol (2.15) | 2.15 | 80 |
| 108 | Xylene | 0.2 | 4.0 | Diphenylamine (2.0) | 2.0 | <50 |
| 109 | Xylene | 0.2 | 4.0 | Phenylacetonitrile (2.0) | 2.0 | <50 |
| 110 | Xylene | 0.2 | 4.0 | Diethyl malonate (2.0) | 2.0 | <50 |

[a]Triphenylmethanol has been dissolved in a minimum amount of THF prior to the addition to the reaction mixture.
[b]NaOtBu (3 equiv.) has been added prior to the acylation reaction.

TABLE 5

Variation of conditions in the protonation/reduction step by the addition of metal, alcohol, cosolvent, etc.; Alcohol used: tert-butanol (1).

| | | | | Protonation/Reduction Step | | | |
|---|---|---|---|---|---|---|---|
| Entry | Solvent | Conc. [mol/kg] | Na [eq.] | Additive [eq.] | 1 [eq.] | Additive[a] [eq.] | TMBCl [eq.] | Yield [%] |
| 111 | Toluene | 0.2 | 4.15 | — | 2.0 | DMA (1.0) Alcohol (0.15) | 2.15 | 73 |
| 112 | Toluene | 0.4 | 4.15 | — | 2.0 | DMA (2.0) | 2.0 | 73 |
| 113 | Toluene | 0.4 | 4.15 | — | 2.0 | DMPU (2.0) | 2.0 | 69 |
| 114 | Toluene | 0.4 | 4.15 | — | 2.15 | DMPU (2.0) | 2.15 | 74 |
| 115 | Toluene | 0.2 | 4.15 | — | 2.0 | Diglyme (1.0) Alcohol (0.15) | 2.15 | 77 |

[b]Additive has been added after the reduction/protonation step, followed by additional heating of the reaction mixture.

TABLE 6

Variation of conditions in the protonation/reduction step by the addition of metals, cosolvents, etc.; Alcohol used: 3-methyl-3-pentanol (2).

| | | | | Protonation/Reduction Step | | | |
|---|---|---|---|---|---|---|---|
| Entry | Solvent | Conc. [mol/kg] | Na [eq.] | Additive[a] [eq.] | 2 [eq.] | Additive[b] [eq.] | TMBCl [eq.] | Yield [%] |
| 116 | Toluene | 0.4 | 4.15 | — | 2.0 | Li (0.5) Alcohol (0.3) | 2.15 | 53 |
| 117 | Toluene | 0.4 | 4.15 | — | 2.0 | Li (0.3) | 2.65 | 79 |
| 118 | Toluene | 0.4 | 4.1 | — | 2.1 | LiAlH$_4$ (0.2) | 2.0 | 68[d] |
| 119 | Toluene | 0.4 | 4.1 | DME (1.0) | 2.1 | — | 2.0 | 84 |

TABLE 6-continued

Variation of conditions in the protonation/reduction step by the addition of metals, cosolvents, etc.; Alcohol used: 3-methyl-3-pentanol (2).

| | | | Protonation/Reduction Step | | | | |
|---|---|---|---|---|---|---|---|
| Entry | Solvent | Conc. [mol/kg] | Na [eq.] | Additive[a] [eq.] | 2 [eq.] | Additive[b] [eq.] | TMBCl [eq.] | Yield [%] |
| 120 | Toluene | 0.4 | 4.1 | — | 2.1 | Li (0.3) Alcohol (0.3) | 2.0 | 67[g] |
| 121 | Toluene | 0.7 | 4.0[c] | KOH (0.18) | 2.0 | — | 2.0 | 81 |
| 122 | Toluene | 0.7 | 4.0[c] | KOtBu (0.1) | 2.0 | — | 2.0 | 60 |
| 123 | Mesitylene | 0.4 | 4.1 | — | 2.1[e] | — | 2.0 | 66[d] |
| 124 | Toluene | 0.4 | 4.15 | — | 2.0 | Diglyme (2.0) Alcohol (0.15) | 2.15 | —[f] |
| 125 | Toluene | 0.4 | 4.15 | — | 2.15 | LiCl (2.0) NaOtBu (0.5) | 2.15 | —[f] |

[a] Additive has been added prior to the reduction/protonation step.
[b] Additive has been added after the reduction/protonation step, followed by additional heating of the reaction mixture.
[c] Metallation reaction has been catalyzed by the addition of 0.02 equiv. of alcohol.
[d] Prior to the oxidation reaction the pH has been adjusted to four.
[e] The protonation/reduction step has been performed at 150° C.
[f] Yield not determined.
[g] Yield of pure bis(2,4,6-trimethylbenzoyl)phenylphosphine oxide after purification by flash chromatography.

TABLE 7

Variation of conditions in acylation step:
Alcohol 1: tert-butanol;
Alcohol 2: 3-methyl-3-pentanol.

| | | | | | Acylation Step | | |
|---|---|---|---|---|---|---|---|
| Entry | Solvent | Conc. [mol/kg] | Na [eq.] | Alcohol [eq.] | TMBCl [eq.] | Temp [° C.] | Yield [%] |
| 126 | Toluene | 0.4 | 4.15 | 1 (2.15) | 1.7 | 30-40 | 45 |
| 127 | Toluene | 0.4 | 4.15 | 1 (2.15)[a] | 2.0 | 20-25 | 77 |
| 128 | Toluene | 0.4 | 4.15 | 1 (2.15)[a] | 2.0 | 50-60 | 77 |
| 129 | Toluene | 0.4 | 4.15 | 1 (2.15)[a] | 2.3 | 30-40 | 73 |
| 130 | Toluene | 0.4 | 4.15 | 1 (2.15)[a] | 2.5 | 30-40 | 70 |
| 131 | Toluene | 0.7 | 4.15 | 2 (2.15)[a] | 2.2 | 30-40 | 75 |
| 132 | Toluene | 0.4 | 4.4 | 2 (2.05) | 2.5[b] | 30-40 | 74 |
| 133 | Toluene | 0.4 | 4.15 | 2 (2.15) | 2.6[b]c] | 30-40 | 87 |

[a] 0.15 equiv. of alcohol added prior to the metallation of PhPCl₂ with sodium metal.
[b] The pH has been adjusted to four prior to the oxidation reaction.
[c] The oxidation has been performed with 1.5 equiv. of peracetic acid solution instead of 30% aqueous H₂O₂.

TABLE 8

Variation of conditions in the oxidation step:
Alcohol 2: 3-methyl-3-pentanol;
Concentration: 0.4 mol/kg [mol PhPCl₂/total weight of metallation reaction] in toluene.

| | | | | | Oxidation Step | | |
|---|---|---|---|---|---|---|---|
| Entry | Metal total [eq.] | Alcohol 2 [eq.] | TMBCl [eq.] | pH | Oxidant [eq.] | pH | Yield [%] |
| 134 | 4.15 | 2.15 | 2.15 | — | H₂O₂ (3.0) | — | 80 |
| 140[a] | 4.1 | 2.1 | 2.0 | — | H₂O₂ (1.1) | — | 75 |
| 135 | 5.0 | 3.0 | 2.15 | 12 | H₂O₂ (3.0) | 4.5-5 | 21 |
| 136 | 4.65[b] | 2.3 | 2.15 | 12 | H₂O₂ (3.0) | 4 | 53 |
| 137 | 4.5 | 2.1 | 2.15 | 8-10 | H₂O₂ (3.0) | 4 | 64 |
| 138 | 4.45[c] | 2.0 | 2.65 | 3 | H₂O₂ (2.0) | 2.5-3 | 79-80 |
| 139 | 4.3 | 2.0 | 2.5 | 3 | H₂O₂ (2.0) | 3-3.5 | 79-83 |
| 141 | 4.15 | 2.15 | 2.15 | 3.5 | CH₃CO₃H (1.5) | 3 | 86 |
| 142 | 4.15 | 2.15 | 2.15[d] | 2-2.5 | H₂O₂ (1.5) | 2.5-3 | 83 |
| 143 | 4.15 | 2.15 | 2.15 | 3 | t-BuOOH (1.5) | 4 | 75 |

TABLE 8-continued

Variation of conditions in the oxidation step:
Alcohol 2: 3-methyl-3-pentanol;
Concentration: 0.4 mol/kg [mol PhPCl$_2$/total
weight of metallation reaction] in toluene.

| | | | | | Oxidation Step | | |
|---|---|---|---|---|---|---|---|
| Entry | Metal total [eq.] | Alcohol 2 [eq.] | TMBCl [eq.] | pH | Oxidant [eq.] | pH | Yield [%] |
| 144 | 4.4 | 2.05 | 2.5[d] | 2 | H$_2$O$_2$ (1.5) | 2.5 | 74 |
| 145 | 4.15 | 2.15 | 2.6[d] | 2 | CH$_3$CO$_3$H (1.5) | 2.5 | 87 |

[a]Conc. = 0.7 mol/kg.
[b]4.15 eq. Na - addition of 0.5 eq. Li after the protonation/reduction step.
[c]4.15 eq. Na - addition of 0.3 eq. Li after the protonation/reduction step.
[d]pH has been adjusted after the acylation reaction to the given value by the addition of 1M HCl solution.

Example 2

Preparation of bis(2,4,6-trimethylbenzoyl)phenylphosphine Oxide Using TMEDA, and Tert-butanol as Proton Source a) Metallation of P,P-dichlorophenylphosphine Excluding moisture by an argon atmosphere, sodium lumps (20.61 g, 0.896 mol) are suspended at room temperature in a mixture of toluene (870 g) and TMEDA (N,N,N',N'-tetramethylethylenediamine) (31.23 g, 0.268 mol). This mixture is heated up to reflux with vigorous stirring starting as soon as the temperature reaches 98° C. After formation of a fine sodium suspension P,P-dichlorophenylphosphine (40.10 g, 0.224 mol) is dropwise added over one hour under vigorous stirring. Heating under reflux for an additional 22 h leads to a yellow precipitate.

b) Protonation/Reduction

The yellow suspension is dropwise treated with tert-butanol (33.20 g, 0.448 mol) over one hour at 98-110° C. Stirring is continued under reflux until all of the sodium is used up.

c) Acylation and Neutralisation of TMEDA

To the resulting thin, yellow supension is added 2,4,6-trimethylbenzoyl chloride (82.12 g, 0.450 mol) at such a rate that the temperature is kept at 35-37° C. The mixture is then stirred for another hour at 35-37° C.

Concentrated H$_2$SO$_4$ (27.46 g, 0.270 mol) is dropwise added at room temperature under vigorous stirring at such a rate that the temperature is kept below 40° C. Stirring is continued at room temperature for 10 min.

d) Oxidation using 30% H$_2$O$_2$ at 40-50° C.

To the resulting, thin, light yellow suspension is dropwise added 30% hydrogen peroxide (76.16 g, 0.672 mol) at such a rate that the temperature is kept at 40-50° C. Stirring is continued for 1-2 h at 40-50° C. The light yellow suspension is treated with 250 g of 5% aqueous NaHCO$_3$, and then stirred for 5 min at 40-50° C. The phases are separated and the organic phase washed with water (2×250 g). After evaporation of toluene, heptane (150 g) is added, the mixture heated up to 80° C. and then cooled to room temperature. The resulting solid is collected and washed with heptane (2×60 g). 70.4 g (75%) of bis(2,4,6-trimethylbenzoyl)phenylphosphine oxide are obtained as light yellow powder with a melting point of 130-131° C.

Example 3

Preparation of bis(2,4,6-trimethylbenzoyl)phenylphosphine Oxide Using Catalytic Amounts of Sodium Hydroxide During Metallation, and Tert-butanol as Proton Source a) Metallation of P,P-dichlorophenylphosphine in Toluene at 98-110° C.

Excluding moisture by an argon atmosphere, sodium lumps (21.85 g, 0.940 mol) are suspended at room temperature in toluene (430 g), together with sodium hydroxide (0.09 g). This mixture is heated up to reflux with vigorous stirring starting as soon as the temperature reaches 98° C. After formation of a fine sodium suspension P,P-dichlorophenylphosphine (41.80 g, 0.224 mol) is dropwise added over 4 h under vigorous stirring. Heating is continued under reflux for ca. 5 h until all P,P-dichlorophenylphosphine has reacted (check by $^{31}$P-NMR).

b) Protonation/Reduction

The resulting greenish grey suspension is dropwise treated with tert-butanol (33.40 g, 0.448 mol) over 40 min at 98-110° C. Stirring is continued under reflux until all sodium is used up (ca. one hour).

c) Acylation

To the resulting thin, yellow suspension is added 2,4,6-trimethylbenzoyl chloride (82.53 g, 0.448 mol) at such a rate that the temperature is kept at 35-37° C. The mixture is then stirred for another hour at 35-37° C.

d) Oxidation using 30% H$_2$O$_2$ at 40-50° C.

To the resulting, thin, yellow-orange suspension is dropwise added 30% hydrogen peroxide (30.50 g, 0.268 mol) at such a rate that the temperature is kept between 75-80° C. Stirring is continued for 1-2 h at 80° C. The light yellow suspension is treated with 150 g of 1% aqueous NaHCO$_3$, and then stirred for 15 min at 65-70° C. The two phases are separated and the organic phase washed with water (3×80 g). After evaporation of toluene, heptane (150 g) is added, the mixture heated up to 98° C., stirred during 15 min, and then cooled to room temperature. The resulting solid is collected and washed with heptane (2×60 g). 73.8 g (78%) of bis(2,4,6-trimethylbenzoyl)phenylphosphine oxide are obtained as light yellow powder with a melting point of 130-131° C.

Example 4

Preparation of
bis(2,4,6-trimethylbenzoyl)phenylphosphine Oxide
Using Catalytic Amounts of 3-methyl-3-pentanol
During Metallation, and 3-methyl-3-pentanol as
Proton Source a) Metallation of P,P-dichlorophenylphosphine in Toluene at 98-110° C.

Excluding moisture by an argon atmosphere, sodium lumps (23.40 g, 1.008 mol) are suspended at room temperature in toluene (280 g), together with 3-methyl-3-pentanol (0.26 g). This mixture is heated up to reflux with vigorous stirring starting as soon as the temperature reaches 98° C. After formation of a fine sodium suspension P,P-dichlorophenylphosphine (44.50 g, 0.246 mol) is dropwise added over 4.5 h under vigorous stirring. Heating is continued under reflux for ca. 1 h until all P,P-dichlorophenylphosphine has reacted (check by $^{31}$P-NMR).

b) Protonation/Reduction

The resulting greenish grey suspension is dropwise treated with 3-methyl-3-pentanol (53.60 g, 0.514 mol) over 40 min at 98-110° C. Stirring is continued under reflux until all sodium is used up (ca. one hour).

c) Acylation

To the resulting thin, yellow suspension is added 2,4,6-trimethylbenzoyl chloride (91.62 g, 0.492 mol) at such a rate that the temperature is kept at 35-37° C. The mixture is then stirred for another hour at 35-37° C.

d) Oxidation using 30% $H_2O_2$ at 40-50° C.

To the resulting thin, yellow-orange suspension is first dropwise added $H_2O$ (125 g) at room temperature during 10 min. The reaction mixture is heated up to 60° C. followed by the addition of 30% hydrogen peroxide (30.62 g, 0.270 mol) at such a rate that the temperature is kept between 75-80° C. Stirring is continued for 30 min at 80° C. and the aqueous phase separated at 50° C. The light yellow suspension is treated with 77 g of 1% aqueous $NaHCO_3$, and then stirred for 5 min at 40-50° C. The two phases are separated and the organic phase washed with water (3×36 g). After evaporation of toluene and 3-methyl-3-pentanol, heptane (132 g) is added, the mixture heated up to 80° C., stirred during 15 min, and then slowly cooled to room temperature. The resulting solid is collected and washed with heptane (2×25 g). 77.6 g (75.4%) of bis(2,4,6-trimethylbenzoyl)phenylphosphine oxide are obtained as light yellow powder with a melting point of 130-131° C.

Example 5

Preparation of
bis(2,4,6-trimethylbenzoyl)phenylphosphine Oxide
Using Catalytic Amounts of Potassium Tert-butoxide
During Metallation, and 3-methyl-3-pentanol as
Proton Source a) Metallation of P,P-dichlorophenylphosphine in Toluene at 98-110° C.

Excluding moisture by an argon atmosphere, sodium lumps (22.66 g, 0.984 mol) are suspended at room temperature in toluene (280 g), together with potassium tert-butoxide (2.77 g, 0.024 mol). This mixture is heated up to reflux with vigorous stirring starting as soon as the temperature reaches 98° C. After formation of a fine sodium suspension P,P-dichlorophenylphosphine (44.50 g, 0.246 mol) is dropwise added over 9 h under vigorous stirring. Heating is continued under reflux for 15 min until all P,P-dichlorophenylphosphine has reacted (check by $^{31}$P-NMR).

b) Protonation/Reduction

The resulting yellow suspension is dropwise treated with 3-methyl-3-pentanol (51.29 g, 0.492 mol) over 1 h at 98-110° C. Stirring is continued under reflux until all sodium is used up (ca. one hour).

c) Acylation

To the resulting thin, yellow suspension is added 2,4,6-trimethylbenzoyl chloride (91.62 g, 0.492 mol) at such a rate that the temperature is kept at 35-37° C. The mixture is then stirred for another hour at 35-37° C.

d) Oxidation using 30% $H_2O_2$ at 40-50° C.

To the resulting thin, yellow-orange suspension is dropwise added $H_2O$ (125 g) at room temperature during 10 min. The reaction mixture is heated up to 60° C. followed by the addition of 30% hydrogen peroxide (30.62 g, 0.270 mol) at such a rate that the temperature is kept between 75-80° C. Stirring is continued for 2 h at 80° C. followed by the separation of the aqueous phase at 50° C. The resulting light yellow organic phase is stirred together with 77 g of 1% aqueous $NaHCO_3$ for 5 min at 40-50° C. The two phases are separated and the organic phase washed with water (3×36 g). After evaporation of toluene and 3-methyl-3-pentanol, heptane (132 g) is added, the mixture heated up to 80° C., stirred during 15 min, and then slowly cooled to room temperature. The resulting solid is collected and washed with heptane (2×25 g). 80.3 g (78%) of bis(2,4,6-trimethylbenzoyl)phenylphosphine oxide are obtained as light yellow powder with a melting point of 130-131° C.

Example 6

Preparation of
bis(2,4,6-trimethylbenzoyl)phenylphosphine Oxide
Using Catalytic Amounts of Potassium Tert-butoxide
During Metallation, and 3-methyl-3-pentanol as
Proton Source a) Metallation of P,P-dichlorophenylphosphine in Toluene at 110° C.

Excluding moisture by an argon atmosphere, potassium tert-butoxide (2.84 g, 24.6 mmol) is shortly stirred together with toluene (280 g) at room temperature. Stirring is stopped, and small sodium lumps (23.51 g, 1.021 mol) are added. The reaction mixture is heated up to 105° C. without stirring and kept at this temperature until all sodium is molten. Vigorous stirring is then started and continued until a fine sodium suspension is formed. P,P-dichlorophenylphosphine (44.47 g, 0.246 mol) is dropwise added to the suspension over 9 h at 10° C. under vigorous stirring. Heating is continued for 15 min until all P,P-dichlorophenylphosphine has reacted (check by $^{31}$P-NMR).

b) Protonation/Reduction

The resulting yellow suspension is dropwise treated with 3-methyl-3-pentanol (55.14 g, 0.529 mol) over 4 h at 110° C. Stirring is continued at 110° C. until all sodium is used up (ca. 15 min).

c) Acylation

To the resulting light yellow suspension is added 2,4,6-trimethylbenzoyl chloride (91.7 g, 0.492 mol) over 3 h at a temperature of 35-37° C. The mixture is then stirred for another hour at 35-37° C.

d) Oxidation using 30% $H_2O_2$ at 40-50° C.

To the resulting thin, yellow suspension is dropwise added $H_2O$ (155 g) at 35-37° C. during 30 min. The aqueous phase is then separated from the reaction mixture followed by treatment with an additional amount of $H_2O$ (45 g). After stirring for 5 min at 35-37° C. the reaction mixture is heated up to 60° C. followed by the addition of 30% hydrogen peroxide (27.86 g, 0.246 mol) during 2 h at such a rate that the temperature is kept between 78-82° C. Stirring is continued for 2 h at 78-82° C. followed by the separation of the aqueous phase at 65-70° C. The resulting light yellow organic phase is washed with water (3×36 g) at 65-70° C. After evaporation of toluene and 3-methyl-3-pentanol, heptane (100 g) is added under stirring during one hour at 78-82° C., and the mixture slowly cooled to room temperature under stirring. The resulting solid is collected and washed with heptane (2×25 g). 80 g (78%) of bis(2,4,6-trimethylbenzoyl)phenylphosphine oxide are obtained as light yellow powder with a melting point of 130-131° C.

Example 7

Preparation of bis(2,4,6-trimethylbenzoyl)phenylphosphine Oxide Using Catalytic Amounts of Potassium Hydroxide Together with 3-methyl-3-pentanol During Metallation, and 3-methyl-3-pentanol as Proton Source a) Metallation of P,P-dichlorophenylphosphine in Toluene at 98-110° C.

Excluding moisture by an argon atmosphere, sodium lumps (22.85 g, 0.984 mol) are suspended at room temperature in toluene (280 g), together with potassium hydroxide (1.61 g, 24.6 mmol) and 3-methyl-3-pentanol (2.54 g, 24.6 mmol). This mixture is heated up to reflux with vigorous stirring starting as soon as the temperature reaches 98° C. After formation of a fine sodium suspension P,P-dichlorophenylphosphine (44.93 g, 0.246 mol) is dropwise added over 2 h under vigorous stirring. Heating is continued under reflux for 1 h until all P,P-dichlorophenylphosphine has reacted (check by $^{31}$P-NMR).

b) Protonation/Reduction

The resulting orange suspension is dropwise treated with 3-methyl-3-pentanol (50.78 g, 0.492 mol) over 1 h at 98-110° C. Stirring is continued under reflux until all sodium is used up (ca. one hour).

c) Acylation

To the resulting thin, yellow suspension is added 2,4,6-trimethylbenzoyl chloride (91.62 g, 0.492 mol) at such a rate that the temperature is kept at 35-37° C. The mixture is then stirred for another hour at 35-37° C.

d) Oxidation using 30% $H_2O_2$ at 40-50° C.

To the resulting thin, yellow-orange suspension is dropwise added $H_2O$ (125 g) at room temperature during 10 min. The reaction mixture is treated with 30% hydrogen peroxide (41.83 g, 0.369 mol) at such a rate that the temperature is kept between 40-50° C. Stirring is continued for 1 h at 70° C. and the aqueous phase separated at room temperature. The resulting light yellow suspension is washed with 150 ml of 5% aqueous $NaHCO_3$, and twice with 100 ml of $H_2O$. The combined aqueous phases are extracted with toluene (100 ml). Drying of the combined organic phases over $Na_2SO_4$, evaporation of toluene and 3-methyl-3-pentanol provides a yellow solid (98.0 g). Heptane (132 g) is added, the mixture heated up to 80° C., stirred during 15 min, and then slowly cooled to room temperature. The resulting solid is collected and washed with heptane (2×40 g). 79.3 g (77%) of bis(2,4,6-trimethylbenzoyl)-phenylphosphine oxide are obtained as light yellow powder with a melting point of 130-131° C.

Example 8

Preparation of bis(2,4,6-trimethylbenzoyl)phenylphosphine Oxide Using Catalytic Amounts of Potassium During Metallation, and 3-methyl-3-pentanol as Proton Source a) Metallation of P,P-dichlorophenylphosphine in Toluene at 98-110° C.

Excluding moisture by an argon atmosphere, sodium lumps (22.60 g, 0.984 mol) and potassium lumps (0.96 g, 24.6 mmol) are suspended at room temperature in toluene (280 g), together with 3-methyl-3-pentanol (0.25 g, 2.46 mmol). This mixture is heated up to reflux with vigorous stirring starting as soon as the temperature reaches 98° C. After formation of a fine sodium/potassium suspension P,P-dichlorophenylphosphine (44.50 g, 0.246 mol) is dropwise added over 4 h under vigorous stirring. Heating is continued under reflux for ca. 2 h until all of P,P-dichlorophenylphosphine has reacted (check by $^{31}$P-NMR).

Steps b)-d) have been performed as described in Example 4.

Example 9

Preparation of bis(2,4,6-trimethylbenzoyl)phenylphosphine Oxide with Partial Removal of 3-methyl-3-pentanol During the Acylation Step a) Metallation of P,P-dichlorophenylphosphine in Toluene at 98-110° C.

Excluding moisture by an argon atmosphere, sodium lumps (22.99 g, 0.984 mol), three times washed with toluene, are suspended at room temperature in toluene (280 g), together with potassium tert-butoxide (2.77 g, 0.024 mol). This mixture is heated up to reflux with vigorous stirring starting as soon as the temperature reaches 100° C. After formation of a fine sodium suspension, P,P-dichlorophenylphosphine (44.50 g, 0.246 mol) is dropwise added over 3-4 h under vigorous stirring. Heating is continued under reflux for 1 h 15 min until all P,P-dichlorophenylphosphine has reacted (check by $^{31}$P-NMR).

b) Protonation/Reduction

The resulting yellow suspension is dropwise treated with 3-methyl-3-pentanol (51.2 g, 0.492 mol) over 1 h 15 min at 98-110° C. Stirring is continued under reflux until all sodium is used up (1 h 30 min). The resulting thin, yellow suspension is kept at room temperature under argon overnight.

c) Acylation 2,4,6-trimethylbenzoyl chloride (45.81 g, 0.246 mol) is added dropwise to the yellow suspension at such a rate that the temperature is kept at 35-37° C. (50 min). The following procedure is now repeated five times: a) addition of toluene, b) distillation of a mixture of toluene/3-methyl-3-pentanol from the reaction mixture under reduced pressure (280 mbar) at 65-75° C. (total amount of toluene added: 830 ml; total amount of liquid removed: 830 ml). Another equivalent of 2,4,6-trimethylbenzoyl chloride (45.81 g, 0.246 mol) is now added dropwise to the yellow suspension at such a rate that the temperature is kept at 35-37° C. (2 h 20 min). The mixture is then stirred for an additional 35 min at 35-37° C.

d) Oxidation using 30% $H_2O_2$ at 40-50° C.

To the resulting thin, yellow-orange suspension is dropwise added $H_2O$ (125 g) at room temperature during 5 min. The reaction mixture is heated up to 60° C. followed by the addition of 30% hydrogen peroxide (41.9 g, 0.370 mol) at such a rate that the temperature is kept between 75-80° C. Stirring is continued for 1 h 15 min at 70° C. The reaction mixture is extracted once with 150 ml 5% $NaHCO_3$ and two times with 150 ml water. Drying of the organic layer over $Na_2SO_4$ and evaporation provides a yellowish oil (103 g). The crude material is crystallized from heptane (132 ml), providing 80.5 g (77%) of bis(2,4,6-trimethylbenzoyl)phenylphosphine oxide as light yellow powder.

Example 10

Preparation of bis(2,4,6-trimethylbenzoyl)-2,4-dipentoxyphenylphosphine oxide

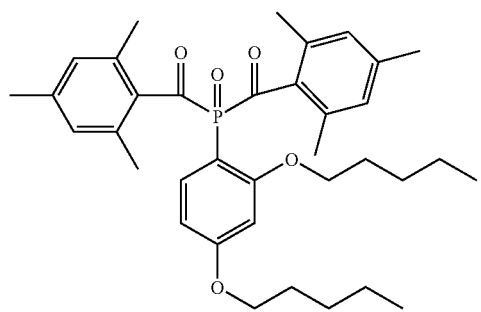

formula I''', $R_1$=2,4-dipentoxyphenyl, $R_2$, $R_2'$=mesityl;

a) Metallation of P,P-dichloro-2,4-dipentoxyphenylphosphine in Toluene at 98-1 10° C.

Excluding moisture by an argon atmosphere, sodium lumps (3.1 g, 135 mmol), three times washed with toluene, are suspended at room temperature in toluene (130 ml), together with potassium tert-butoxide (0.39 g, 34.0 mmol). This mixture is heated up to reflux with vigorous stirring starting as soon as the temperature reaches 100° C. After formation of a fine sodium suspension, P,P-dichloro-2,4-dipentoxyphenylphosphine (11.87 g, 34.0 mmol) dissolved in 20 ml toluene is added dropwise over 34 h under vigorous stirring. Heating is continued under reflux for 17 h.

b) Protonation/Reduction

The resulting dark violet suspension is dropwise treated with 3-methyl-3-pentanol (6.91 g, 68 mmol) over one hour at 98-110° C. Stirring is continued under reflux until all sodium is used up (24 h).

c) Acylation

To the resulting grey/black suspension is added 2,4,6-trimethylbenzoyl chloride (12.34 g, 68 mmol) at such a rate that the temperature is kept at 35-37° C. The mixture is then stirred for another hour at 35-37° C.

d) Oxidation using 30% $H_2O_2$ at 40-50° C.

To the resulting green/black suspension is dropwise added $H_2O$ (10 g) at 50° C. within 5 min. The reaction mixture is kept at 50-60° C. followed by the addition of 30% hydrogen peroxide (5.73 g, 51 mmol) at such a rate that the temperature is kept between 50-60° C. Stirring is continued for one hour at 50-60° C. The reaction mixture is extracted once with 5% aqueous $NaHCO_3$ and water. Drying of the organic phase over $Na_2SO_4$ and evaporation provides 24.0 g of a yellowish oil. One gram of crude material is purified by preparative liquid chromatography (heptane/ethyl acetate 60:40). After evaporation 230 mg of bis(2,4,6-trimethylbenzoyl)-2,4-dipentoxyphenylphosphine oxide are obtained as a yellow oil. The calculated overall yield of the title product is 28%.

Example 11

I) Preparation of Pentaphenylcyclopentaphosphane $(PhP)_5$ $(PhP)_5$ has been prepared as described in the Int. Patent Application PCT/EP 03/50873 by suspending sodium pieces in a mixture of toluene/TMEDA and adding P,P-dichlorophenylphosphine.

II) Preparation of bis(2,4,6-trimethylbenzoyl)phenylphosphine oxide from Pentaphenylcyclopentaphosphane $(PhP)_5$, with Tert-butanol as Proton Source a) Metallation and Protonation of Pentaphenylcyclopentaphosphane $(PhP)_5$ Excluding moisture by an argon atmosphere, $(PhP)_5$ (0.26 g, 0.48 mmol) is dissolved in 30 ml of dry toluene. Sodium lumps (0.11 g, 9 4.8 mmol) are added at room temperature and the mixture is heated up to reflux with vigorous stirring starting as soon as the sodium is melted. The resulting suspension is treated with tert-butanol (0.356 g, 4.8 mmol) at 98-110° C. Stirring is continued under reflux until all of the $(PhP)_5$ is used up and $PhPH_2$ is formed. Acylation and oxidation have been performed as described in Example 1.

Example 12

I) Preparation of Disodium (Diphenyldiphosphanediide) of Formula $[Na(dme)_3]^+[Na_5(P_2Ph_2)_3(dme)_3]^-$ Disodium (diphenyldiphosphanediide) of the formula $[Na(dme)_3]^+[Na_5(P_2Ph_2)_3(dme)_3]^-$ has been prepared as described in the Int. Patent Application PCT/EP 03/50873 by suspending sodium pieces in a mixture of toluene/DME and adding P,P-dichlorophenylphosphine.

II) Acylation of $[Na(dme)_3]^+[Na_5(P_2Ph_2)_3(dme)_3]^-$.

Crystalline $[Na(dme)_3]^+[Na_5(P_2Ph_2)_3(dme)_3]^{31}$ (3 g) is suspended in toluene (20 mL) and 2,4,6-trimethylbenzoyl chloride (1.5 fold excess) is added such that the reaction temperature does not rise above 40° C. The immediate precipitation of NaCl is observed. The slightly yellow colored solution contains about 60 mol % of acylated products and 40 mol % of cyclooligophosphanes. The fraction of the acylated products is composed of approximately 60 mol % PhP (COMes)$_2$, 30 mol % of Ph$_2$P$_2$(COMes)$_2$ and 10 mol % of the (E$_1$Z)-isomers of (PhPCOMes)$^-$ in a molar ratio of 2:1. The fraction of the cyclophosphanes consists of 85 mol % (PhP)$_5$ and 15 mol % (PhP)$_4$.

Example 13

Preparation of bis(2,4,6-trimethylbenzoyl)phenylphosphane Oxide without a Proton Source a) Metallation of P,P-dichlorophenylphosphine Excluding moisture by an argon atmosphere, sodium lumps (2.58 g, 112 mmol) are suspen-ded at room temperature in a mixture of toluene (17.4 g) and TMEDA (N,N,N',N'-tetra-methylethylenediamine) (1.62 g, 14.0 mmol). This mixture is heated up to reflux with vigorous stirring starting as soon as the sodium is melted. After formation of a fine sodium suspension, P,P-dichlorophenylphosphine (5 g, 28 mmol) is added dropwise over one hour under vigorous stirring. Heating under reflux for an additional 2.5 h leads to a green/yellow suspension.

b) Acylation

To the resulting thin, green/yellow supension is added 2,4,6-trimethylbenzoyl chloride (10.2 g, 56 mmol) at 0-10° C. The mixture is then stirred for another 1.5 hour at 0-10° C.

c) Oxidation using H$_2$O$_2$ at 80° C.

30% hydrogen peroxide (6.0 g, 53 mmol) is added dropwise to the resulting suspension at room temperature. The mixture is heated up to 80° C. and stirring is continued for 1-2 h. The light yellow suspension is washed with water (2×50 g). After evaporation of toluene, heptane (35 g) is added, the mixture heated up to 80° C. and then cooled to room temperature. The resulting solid is collected and washed with heptane (2×15 g). 3.75 g (32%) of bis(2,4,6-trimethylbenzoyl)phenylphosphane oxide are obtained as light yellow powder with a melting point of 130-131° C.

Example 14

Preparation of bis(2,4,6-trimethylbenzoyl)phenylphosphine Oxide Starting from P,P-dichlorophenylphosphine Oxide a) Metallation of P,P-dichlorophenylphosphine Oxide Excluding moisture by an argon atmosphere, sodium lumps (2.3 g, 0.10 mol) are suspended at room temperature in a mixture of xylene (50 ml) and TMEDA (N,N,N',N'-tetramethylethylenediamine) (1.47 g, 12.5 mmol). This mixture is heated up to 105-110° C. with vigorous stirring starting as soon as the sodium is melted. After formation of a fine sodium suspension, P,P-dichlorophenylphosphine oxide (4.87 g, 25.0 mmol) is added dropwise over 10 min under vigorous stirring. Heating under reflux for an additional 23 h leads to a yellow precipitate.

b) Acylation

To the resulting yellow supension is added 2,4,6-trimethylbenzoyl chloride (9.13 g, 50 mmol) at 5° C. over 20 min. The mixture is then stirred for another 2 h at 30° C.

c) Oxidation with Hydrogen Peroxide has Been Performed as Described in Example 1.

Example 15

Preparation of (E,Z)-sodium-phenylphospha-2,4,6-trimethylbenzoylenolate

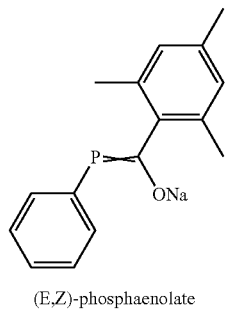

(E,Z)-phosphaenolate a) Metallation of P,P-dichlorophenylphosphine in Toluene at 98-110° C.

Excluding moisture by an argon atmosphere, sodium lumps (6.78 g, 0.295 mol) are suspended at room temperature in toluene (100 ml), together with potassium tert-butoxide (827 mg, 7.37 mmol). This mixture is heated up to reflux with vigorous stirring starting as soon as the temperature reaches 98° C. After formation of a fine sodium suspension P,P-dichlorophenylphosphine (13.2 g, 73.7 mmol) is added during 2 h under vigorous stirring. During the addition, the color of the reaction mixture changed from yellow, to orange, to light yellow and then to gray. Heating is continued under reflux for 6 h until all P,P-dichlorophenylphosphine has reacted (check by $^{31}$P-NMR).

b) Protonation/Reduction

The resulting green-yellow suspension is dropwise treated with tert-butanol (14 ml) in toluene (10 ml) over 3 h at 98-110° C. Stirring is continued under reflux for 2 h.

c) Acylation

To the resulting light yellow suspension is dropwise added 2,4,6-trimethylbenzoyl chloride (12.11 g, 66.3 mmol, 0.9 eq.) at room temperature. The suspension is filtered, washed with toluene (10 ml), and the volume of the filtrate reduced to half by solvent evaporation. A light yellow solid precipitated overnight at −18° C. The solid is separated, washed with hexane (20 ml) and then dried under high vacuum for 12 h, giving 9.13 g product. Additional 3.72 g product is isolated from the filtrate by repeated precipitation. According to $^1$H-NMR the product consists of a mixture of (Z)-enolate/(E)-enolate/tert-butanol 2:1:2 (the (Z)-enolate is tentatively assigned as major isomer).

M.p. (dec.)=156° C. $^{31}$P-NMR(d$_8$-THF): δ=79.9, 56.2* (*=main signal).

$^1$H-NMR (d$_8$-THF; *=minor isomer, tentatively assigned as (E)-enolate; **=signals corresponding to tert-butanol): δ=7.82 (m, 2 H. C$_{Ph}$—H); 7.03 (m, 2 H, C$_{Ph}$—H); 6.92 (m, 2 H), C$_{Ph}$—H); 6.89 (m, 2 H*, C$_{Ph}$—H); 6.86 (m, 1 H. C$_{Ph}$—H); 6.70 (m, 1 H*, C$_{Ph}$—H); 6.67 (s, 2 H, C$_{Mes}$—H); 6.58 (s, 2 H*, C$_{Mes}$—H); 3.26 (s, 1 H**, $^t$BuOH); 2.42 (s, 6 H, Mes o-CH$_3$); 2.21 (s, 6 H*, Mes o-CH$_3$); 2.18 (s, 3 H, Mes p-CH$_3$); 2.12 (s, 3 H*, Mes p-CH$_3$); 1.14 (s, 9 H**, $^t$Bu CH$_3$).

$^{13}$C-NMR (d$_8$-THF): δ=231.7 (d, PCO, J$_{CP}$=53.8 Hz); 220.7 (d, PCO, J$_{CP}$=68.2 Hz); 150.9 (d, Mes C$^1$, $^2$J$_{CP}$=54.3 Hz); 147.7 (d, Mes C$^1$, $^2$J$^{CP}$=47.6 Hz); 135.2 (d, J$_{CP}$=4.7 Hz); 135.0 (d, J$_{CP}$=1.1 Hz); 134.7 (d, J$_{CP}$=1.6 Hz); 134.3 (d, Ph, $J_{CP}$=13.6 Hz); 133.4 (d, Ph, $J_{CP}$=13.8 Hz); 133.2 (d, $J_{CP}$=2.5 Hz); 128.2 (s, Mes $C^3$); 128.1 (s, Mes $C^3$); 127.4 (d, Ph, $J_{CP}$=4.8 Hz); 127.0 (d, $J_{CP}$=5.1 Hz); 124.3 (d, $J_{CP}$=1.2 Hz); 123.9 (d, $J_{CP}$=0.4 Hz); 67.7 (s, $^tBu$); 31.8 (s, $^tBu$ $CH_3$); 21.1 (s, Mes p-$CH_3$); 21.0 (s, Mes p-$CH_3$); 20.3 (s, Mes o-$CH_3$); 20.2 (s, Mes o-$CH_3$).

Example 16

Preparation of 2,4,6-trimethylbenzoyl-2,6-dimethoxybenzoyl-phenylphosphine Oxide

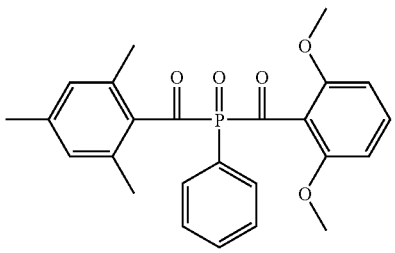

formula I''', $R_1$=phenyl, $R_2$=mesityl, $R_2'$=2,6-dimethoxy;

a) Metallation of P,P-dichlorophenylphosphine in Toluene at 98-110° C.

Excluding moisture by an argon atmosphere, sodium lumps (6.28 g, 0.270 mol) are suspended at room temperature in toluene (150 ml), together with potassium tert-butoxide (782 mg, 6.76 mmol). This mixture is heated up to reflux with vigorous stirring starting as soon as the temperature reaches 98° C. After formation of a fine sodium suspension P,P-dichlorophenylphosphine (12.10 g, 67.6 mmol) is dropwise added over 2 h under vigorous stirring. Heating is continued under reflux for 3 h until all P,P-dichlorophenylphosphine has reacted (check by $^{31}$P-NMR).

b) Protonation/Reduction

The resulting yellow suspension is dropwise treated with 3-methyl-3-pentanol (13.95 g, 135.2 mmol) over 35 min at 98-110° C. Stirring is continued under reflux until all sodium is used up (ca. 1.5 h).

c) Acylation

To the resulting thin, yellow suspension is added 2,4,6-trimethylbenzoyl chloride (10.45 g, 56.1 mmol) in toluene (20 ml) at such a rate that the temperature is kept at 35-37° C. The mixture is then stirred for 1 h 30 min at 35-37° C. 2,6-dimethoxybenzoyl chloride (12.51 g, 56.1 mmol) in toluene (20 ml) is added at room temperature within 10 min and stirring is continued for 1 h 30 min.

d) Oxidation using 30% $H_2O_2$ at Rom Temperature

To the resulting thin, yellow-orange suspension is first dropwise added aqueous 2 M HCl (7 ml) at room temperature. Afterwards, 30% hydrogen peroxide (76.16 g, 0.672 mol) is added at such a rate that the temperature is kept below 35° C. Stirring is continued for 2 h at room temperature. The light yellow suspension is first washed with 42 g of 5% aqueous $NaHCO_3$, and then with water (2×60 ml), and the aqueous phases reextracted with toluene (60 ml). The combined organic phases are dried over $MgSO_4$ and concentrated under vacuum providing a yellow solid. Crystallization (hexane/acetone 2:1) gives 13.4 g (46%) of 2,4,6-trimethylbenzoyl-2,6-dimethoxybenzoyl-phenylphosphine oxide as light yellow solid.

$^{31}$P-NMR ($C_6D_6$): δ=4.6.

$^1$H-NMR ($C_6D_6$): δ=8.45-8.51 (m, 2 H); 7.15-7.20 (m, 3 H); 7.02 (t, 1 H); 6.66 (s, 2 H); 6.14 (d, 2 H); 3.18 (s, 6 H); 2.44 (s, 6 H); 2.09 (s, 3 H).

Example 17

Preparation of 2,4,6-trimethylbenzoyl-pivaloyl-phenylphosphine Oxide

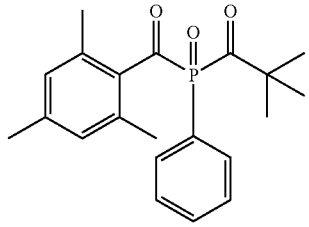

formula I''', $R_1$=phenyl, $R_2$=mesityl, $R_2'$=tert-butyl;

a) Metallation of P,P-dichlorophenylphosphine

Excluding moisture by an argon atmosphere, sodium pieces (2.07 g, 90.3 mmol) are suspended at room temperature in a mixture of toluene (100 ml) and TMEDA (N,N,N',N'-tetramethylethylenediamine) (4 ml). This mixture is heated under reflux and under vigorous stirring. P,P-dichlorophenylphosphane (4.02 g, 22.4 mmol) is added and the suspension is heated under reflux for 5 h until a yellow precipitate is formed.

b) Protonation/Reduction

Excluding moisture by an argon atmosphere, tert-butanol (3.32 g, 44.8 mmol) is added at 100° C. over one hour leading to dissolution of the yellow precipitate. The resulting yellow suspension is further stirred under reflux until all sodium is used up.

c) Acylation and Neutralisation of TMEDA

To the yellow suspension is added dropwise under stirring 2,4,6-trimethylbenzoyl chloride (4.09 g, 22.4 mmol) in toluene (15 ml). The reaction temperature is kept at room temperature. The mixture is then stirred for another two hours at room temperature. Pivaloylchloride (2,2-dimethylpropionyl chloride) (2.71 g, 22.4 mmol) is added dropwise under stirring at room temperature. Concentrated $H_2SO_4$ (1.48 ml, 26.7 mmol) is added dropwise at a temperature below 45° C.

d) Oxidation

To the resulting suspension is added 30% hydrogen peroxide (6.9 ml, 67.6 mmol) under stirring at such a rate that the temperature does not rise above 55° C. Stirring is continued at 40-50° C. for one hour followed by the addition of water (10 ml). The organic phase is separated, washed twice with water and with 10% $NaHCO_3$, and then dried over $Na_2SO_4$. Evaporation yields a yellow oil which is taken up in 30 ml of petroleum ether (40/70)/ethylacetate (9:1). After filtration the title compound is obtained as a yellow solid (5.1 g, 64%) with a melting point of 110-112° C.

$^{31}$P{$^1$H}-NMR ($CDCl_3$): δ=10.0 (t, $^3J_{PH}$=9.85 Hz).

$^1$H-NMR ($CDCl_3$): δ=7.88 (m, 2 H, Ph H$^{(2,6)}$); 7.53 (m, 1 H, Ph H$^{(4)}$); 7.43 (m, 2 H, Ph H$^{(3,5)}$); 6.78 (s, 2 H, Mes H$_{ar}$); 2.24 (s, 3 H, p-$CH_3$); 2.18 (s, 6 H, o-$CH_3$); 1.27 (s, 9 H, $^tBu$).

Example 18

Preparation of 2,4,6-trimethylbenzoyl-2,6-dimethoxybenzoyl-2,4-dipentoxyphenylphosphine Oxide

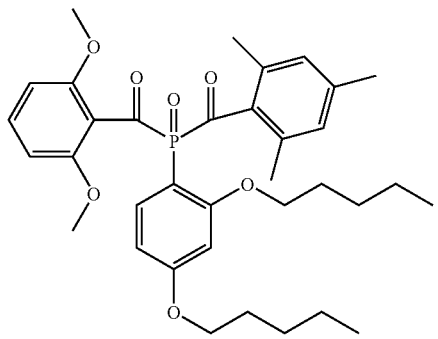

formula I''', $R_1$=2,4-dipentoxyphenyl, $R_2$=mesityl; $R_2$'=2,6-dimethoxyphenyl a) Metallation of P,P-dichloro-2,4-dipentoxyphenylphosphine in Toluene at 98-110° C.

Excluding moisture by an argon atmosphere, sodium lumps (1.55 g, 67.6 mmol), three times washed with toluene, are suspended at room temperature in toluene (70 ml), together with potassium hydroxide (powdered) (0.1 g, 1.7 mmol). This mixture is heated up to reflux with vigorous stirring starting as soon as the temperature reaches 100° C. After formation of a fine sodium suspension, P,P-dichloro-2,4-dipentoxyphenylphosphine (6.6 g, 16.9 mmol) dissolved in 10 ml toluene is added dropwise over 3-4 h under vigorous stirring. Heating is continued under reflux for 1 h 40 min.

b) Protonation/Reduction

The resulting dark violet suspension is dropwise treated with 3-methyl-3-pentanol (3.48 g, 33.8 mmol) over 40 min at 95-110° C. Stirring is continued under reflux until all sodium is used up (24 h).

c) Acylation

To the resulting gray suspension is added 2,4,6-trimethylbenzoyl chloride (1.59 g, 8.7 mmol). at such a rate that the temperature is kept at 35-40° C. (31P-NMR spectra shows no more signal for PhPH$_2$). The mixture is then stirred for another 2 h 30 min at 35-40° C. 2,6-dimethoxybenzoyl chloride [1.94 g, 8.7 mmol; dissolved in toluene/tetrahydrofuran (5 ml/1 ml)] is added at 35-40° C. within 60 min and stirring is continued overnight at 35-40° C. The resulting reaction mixture is treated with an additional amount of 2,6-dimethoxybenzoyl chloride [3.77 g, 16.9 mmol; dissolved in toluene/tetrahydrofuran (5 ml/2 ml)] at 35-40° C. within 30 min. Stirring is continued for nine hours at 35-40° C.

d) Removal of Tetrahydrofuran-oxidation using 30% $H_2O_2$ at 40-50° C.

To the resulting gray suspension is added 50 ml of toluene. Afterwards, 60 ml of solvent (tetrahydrofuran/toluene-mixture) are removed by distillation (100 mbar/40-50° C.). The gray/yellow suspension is diluted with a small amount of toluene (10 ml), and then dropwise treated with $H_2O$ (5 ml) at 50-60° C. within 5 min. Stirring is continued for 10 min at 50-60° C. followed by the addition of 30% hydrogen peroxide (2.87 g, 25.4 mmol) at such a rate that the temperature is kept between 50-60° C. Stirring is continued for 40 min at 50-60° C. The reaction mixture is diluted with water, extracted once with 5% aqueous NaHCO$_3$ and twice with water. Drying of the organic phase over Na$_2$SO$_4$ and evaporation provides 9.3 g of a yellowish oil. Further purification by preparative liquid chromatography (heptane/ethyl acetate 80:20) yields 1.85 g (18%) of pure 2,4,6-trimethylbenzoyl-2,6-dimethoxybenzoyl-2,4-dipentoxyphenylphosphine oxide as a yellow viscous oil.

$^{31}$P-NMR (C$_6$DE): δ=15.7.

$^1$H-NMR (C$_6$D$_6$): δ=8.2-8.3 (dd, 1 H); 7.03 (t, 1 H); 6.7 (s, 2 H); 6.5-6.6 (d, 1 H); 6.4-6.5 (d, 1 H); 6.1-6.2 (d, 2 H); 3.6-3.8 (m, 4 H); 3.28 (s, 6 H); 2.62 (s, 6 H); 2.12 (s, 3 H); 1.6-1.9 (m, 4 H); 1.2-1.5 (m, 8 H); 0.9-1.0 (2 t, 6H).

Example 19

Preparation of bis(pivaloyl)phenylphosphine Oxide

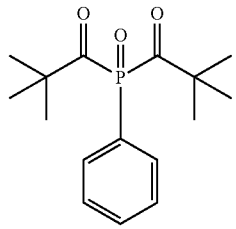

formula I''', $R_1$=phenyl, $R_2$, $R_2$'=tert-butyl;

a) Metallation of Pentaphenylcyclopentaphosphane

Excluding moisture by an argon atmosphere, sodium pieces (0.64 g, 30 mmol), (PPh)$_5$ (1.5 g, 13.88 mmol relative to P) are heated under reflux in a mixture of toluene (50 ml) and of TMEDA (N,N,N',N'-tetramethylethylenediamine) (2 ml) until a yellow precipitate is formed. (PPh)$_5$ has been prepared as described in the Int. Patent Application PCT/EP 03/50873 by suspending sodium pieces in a mixture of toluene/TMEDA and adding P,P-dichlorophenylphosphane.

b) Protonation/Reduction

Excluding moisture by an argon atmosphere, tert-butanol (2.3 g, 2.2 eq.) is added at 100° C. over 30 min leading to dissolution of the yellow precipitate. The resulting yellow suspension is further stirred under reflux until all sodium is used up.

c) Acylation and Neutralisation of TMEDA

Pivaloylchloride (3.68 g, 2.2 eq) is added dropwise under stirring. The reaction temperature is kept below 70° C. Concentrated H$_2$SO$_4$ (0.9 ml) is added dropwise at a temp. below 45° C.

d) Oxidation

30% aqueous hydrogen peroxide (4.3 ml, 42.1 mmol) is added dropwise under stirring at a temperature below 55° C. Stirring is continued at 40-50° C. for one hour followed by the addition of water (10 ml). The organic phase is separated and washed twice with water and with 10% NaHCO$_3$. The organic phase is dried over Na$_2$SO$_4$. After evaporation and washing with hexane the title compound is obtained as a yellow solid (1.84 g, 45%).

$^{31}$P-NMR (CDCl$_3$): δ=16.2 (t. $^3$J$_{PH}$=10.8 Hz).

$^1$H-NMR (CDCl$_3$): δ=7.80 (m, 2 H. Ph H$^{(2,6)}$); 7.57 (m, 1 H. Ph H$^{(4)}$); 7.48 (m, 2 H, Ph H$^{(3,5)}$); 1.27 (s, 18 H, CH$_3$).

$^{13}$C-NMR (CDCl$_3$): δ=132,8 (d, $^4J_{CP}$=3.1 Hz, Ph C$^4$); 132.0 (d, $^2J_{CP}$=8.3 Hz, Ph C$^{2,6}$); 128.7 (d, $^3J_{CP}$=11.4 Hz, Ph C$^{3,5}$); 126.6 (d, $^1J_{CP}$=79.2 Hz, Ph C$^1$); 25.6 (s, CH$_3$).

Comparative Example 5

Ethanol vs. Tert-butanol as Proton Source in the Protonation/Reduction Step

Step b) of Example 2 has been repeated using two equivalents (with regard to P) of ethanol instead of tert-butanol. Gas develops heavily. Selectivity data are obtained by $^{31}$P-NMR. The $^{31}$P-NMR experiments were conducted on Bruker DPX-250 spectrometers.

| 2 eq. (P) Na + 2 eq. tert-BuOH in toluene/TMEDA, after 2.5 h reflux: clear yellow solution. $^{31}$P-NMR(CDCl$_3$): δ = −71.55(d, $J_{PP}$ = 351.4 Hz, HPPhPPhNa); −104.77(d, $J_{PP}$ = 349.3 Hz, HPPhPPhNa); −125.31(s, PhPH$_2$). | 2 eq. (P) Na + 2 eq. EtOH in toluene/TMEDA, after 2.5 h reflux: cloudy orange solution. $^{31}$P-NMR(CDCl$_3$): δ = −25.75(s(br), (PPh)$_4^{2-}$); AK2-spectra(PPh)$_3^{2-}$(−44.04, −44.51, −46.74, −55.33, −57.85), −70.78(d, $J_{PP}$ = 343.3 Hz, HPPhPPhNa); −80.82 bis −89.27(d(br), (PPh)$_4^{2-}$); −101.79(d, $J_{PP}$ = 342.2 Hz, HPPhPPhNa); −124.09(s, PhPHNa), −125.31(s, PhPH$_2$). |
|---|---|

The $^{31}$P-NMR data above clearly indicate that a considerably improved selectivity is obtained in the presence of tert-butanol.

The invention claimed is:
1. A process for the preparation of acylphosphanes of formula I

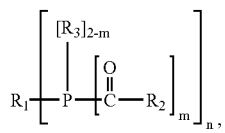

(I)

wherein
n and m are each independently of the other 1 or 2;
R$_1$, if n=1, is
C$_1$-C$_{18}$alkyl, C$_2$-C$_{18}$alkyl which is interrupted by one or several non-successive O atoms, phenyl-C$_1$-C$_4$alkyl, C$_2$-C$_8$alkenyl, phenyl, naphthyl, biphenyl, C$_5$-C$_{12}$cycloalkyl or a 5- or 6-membered O-, S- or N-containing heterocyclic ring, the radicals phenyl, naphthyl, biphenyl, C$_5$-C$_{12}$cycloalkyl or the 5- or 6-membered O-, S- or N-containing heterocyclic ring being unsubstituted or substituted by one to five halogen, C$_1$-C$_8$alkyl, C$_1$-C$_8$alkylthio, C$_1$-C$_8$alkoxy and/or —N(R$_8$)$_2$;
R$_1$, if n=2, is
C$_1$-C$_{18}$alkylene, C$_2$-C$_{18}$alkylene which is interrupted by one or several non-successive O atoms; or R$_1$ is C$_1$-C$_6$alkylene which is substituted by C$_1$-C$_4$alkoxy, phenyl, C$_1$-C$_4$alkylphenyl, phenyl-C$_1$-C$_4$alkyl or C$_1$-C$_6$alkoxyphenyl; or R$_1$ is phenylene or xylylene, which radicals are unsubstituted or substituted by one to three C$_1$-C$_4$alkyl and/or C$_1$-C$_4$alkoxy, or R$_1$ is a

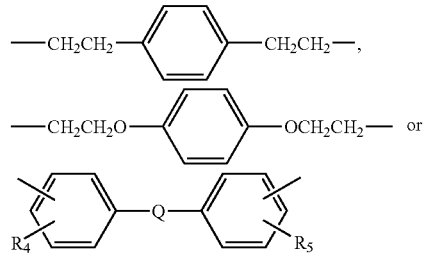

group;
R$_2$ is C$_1$-C$_{18}$alkyl, C$_3$-C$_{12}$cycloalkyl, C$_2$-C$_{18}$alkenyl, phenyl-C$_1$-C$_4$alkyl, phenyl, naphthyl, biphenyl or a 5- or 6-membered O-, S- or N-containing heterocyclic ring, the radicals phenyl, naphthyl, biphenyl or the 5- or 6-membered O-, S- or N-containing heterocyclic ring being unsubstituted or substituted by one to five halogen, C$_1$-C$_8$alkyl, C$_1$-C$_8$alkoxy and/or C$_1$-C$_8$alkylthio;
R$_3$ is C$_1$-C$_{18}$alkyl, C$_2$-C$_{18}$alkyl which is interrupted by one or several non-successive O atoms or which is interrupted by —CO—, —COO—, —OCO—, —OCOO—, —CO—N(R$_9$)—, —N(R$_9$)—CO—, —N(R$_9$)—CO—N(R$_9$)—, —N(R$_9$)—COO—; C$_1$-C$_{18}$ alkyl substituted by —OR$_{10}$, —OCO—R$_{10}$, —COO—R$_{10}$, —N(R$_9$)—CO—R$_{10}$, —CO—N(R$_9$)—R$_{10}$, —C(R$_{11}$)=C(R$_{12}$)—CO—OR$_{10}$ or —C(R$_{11}$)=C(R$_{12}$)-phenyl;
C$_2$-C$_{12}$alkenyl or C$_2$-C$_{12}$alkenyl which is interrupted by one or several non-successive O atoms;
phenyl-C$_1$-C$_4$alkyl, phenyl, naphthyl, biphenyl, C$_5$-C$_{12}$cycloalkyl or a 5- or 6-membered O-, S- or N-containing heterocyclic ring, the radicals phenyl, naphthyl, biphenyl, C$_5$-C$_{12}$cycloalkyl or the 5- or 6-membered O-, S- or N-containing heterocyclic ring being unsubstituted or substituted by one to five halogen, C$_1$-C$_8$alkyl, C$_1$-C$_8$alkylthio C$_1$-C$_8$alkoxy and/or —N(R$_8$)$_2$; or R$_3$ is —CO—OR$_9$ or —CO—N(R$_9$)$_2$;
Q is a single bond, CR$_6$R$_7$, —O— or —S—;
R$_4$ and R$_5$ are each independently of the other hydrogen, C$_1$-C$_4$alkyl or C$_1$-C$_4$alkoxy;
R$_6$ and R$_7$ are each independently of the other hydrogen or C$_1$-C$_4$alkyl;
R$_8$ is C$_1$-C$_{18}$ alkyl, C$_2$-C$_{18}$ alkyl which is interrupted by one or several non-successive O-atoms; or —N(R$_8$)$_2$ forms a 5- or 6-membered O-, S- or N-containing heterocyclic ring;
R$_9$ is hydrogen, C$_1$-C$_{18}$alkyl, C$_2$-C$_{18}$alkyl which is interrupted by one or several non-successive O atoms, C$_3$-C$_{12}$-cycloalkyl, C$_2$-C$_{18}$-alkenyl, phenyl-C$_1$-C$_4$-alkyl, phenyl, naphthyl, pyridyl, the radicals phenyl, naphthyl or pyridyl being unsubstituted or substituted by one to five C$_1$-C$_8$-alkyl, C$_1$-C$_8$-alkoxy, C$_1$-C$_8$-alkylthio and/or halogen; or —N(R$_9$)$_2$ forms a 5- or 6-membered O-, S- or N-containing heterocyclic ring;
R$_{10}$ is C$_1$-C$_{18}$alkyl, C$_2$-C$_{18}$alkyl which is interrupted by one or several non-successive O-atoms, C$_3$-C$_{12}$-cycloalkyl, phenyl-C$_1$-C$_4$-alkyl, C$_2$-C$_{18}$-alkenyl, phenyl, naphthyl or biphenyl, the radicals phenyl-C$_1$-C$_4$-alkyl, phenyl, naphthyl or biphenyl being unsubstituted or substituted by one to five C$_1$-C$_8$-alkyl, C$_1$-C$_8$-alkoxy, C$_1$-C$_8$-alkylthio and/or halogen;

$R_{11}$ is hydrogen or $C_1$-$C_4$-alkyl;
$R_{12}$ is hydrogen or $C_1$-$C_4$-alkyl;
by
(1) reacting a phosphorous halide of formula IIa or a phosphorous halide oxide of formula IIb or a phosphorous halide sulfide of formula IIc

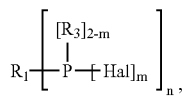  (IIa)

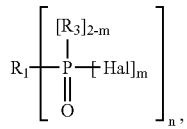  (IIb)

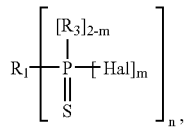  (IIc)

wherein $R_1$, $R_3$, n and m have the meaning cited above and Hal is F, Cl, Br or I;
with an alkali metal in a solvent (metallation) in the presence of a proton source (reduction);
(2) subsequent reaction with m acid halides of formula III

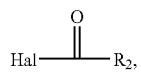  (III)

wherein $R_2$, Hal and m have the meaning cited above.

2. A process according to claim 1, wherein in step (1) the metallation is carried out by reacting a compound of the formula IIa, IIb, or IIc with lithium, sodium or potassium or magnesium in combination with lithium in a solvent.

3. A process according to claim 2, wherein
the alkali metal is sodium;
the proton source is selected from the group consisting of sterically hindered alcohols, trialkylamine hydrohalogenes, bisarylamines, malono nitrile, malonic acid esters, amidine hydrohalogene and carboxylic acids;
the solvent is one or more compounds selected from the group consisting of benzene, toluene, o-, m- or p-xylene, mesitylene, ethylbenzene, diphenylethane, 1,2,3,4-tetrahydronaphthaline (tetraline) and isopropylbenzene (cumol); and
the reaction temperature of step (1) is in the range from −20° C. to +160° C.

4. A process according to claim 3, wherein the sterically hindered alcohol is selected from the group consisting of secondary and tertiary $C_3$-$C_{18}$ alcohols.

5. A process according to claim 1, wherein metallation is carried out in the presence of catalytic amounts of alkali or earth alkali hydroxides or of Na, K or Li alcoholates or of alcohols.

6. A process according to claim 1, wherein the metallation and reduction step is carried out in the presence of an activator.

7. A process according to claim 6, wherein the activator is an amine selected from the group consisting of triethylamine, tributylamine, piperidine, morpholine, N-methylpiperidine, N-methyl morpholine and polyamines.

8. A process according to claim 1 for the preparation of monoacylphosphanes of the formula I'

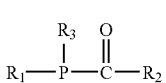  (I')

by
(1) reacting organic phosphorus halides of formula II'

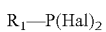  (II')

with an alkali metal in a solvent in the presence of a proton source; and either
(2a) subsequent reaction with an acid halide of formula III'

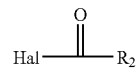  (III')

followed by the reaction with an electrophilic compound $R_3$-Hal, or
(2b) subsequent reaction with with an electrophilic compound $R_3$-Hal followed by the reaction with an acid halide of formula III'

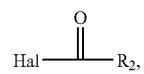  (III')

wherein $R_1$, $R_2$ and $R_3$ and Hal are as defined in claim 1.

9. A process according to claim 1 for the preparation of symmetric bisacylphosphanes of the formula I"

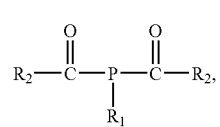  (I")

by
(1) reacting organic phosphorus halides of formula II"

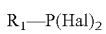  (II")

with an alkali metal in a solvent in the presence of a proton source;
(2) subsequent reaction with an acid halide of formula III"

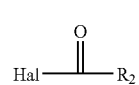  (III")

wherein $R_1$ and $R_2$ and Hal are as defined in claim 1.

10. A process according to claim 1 for the preparation of unsymmetric bisacylphosphanes of the formula I'''

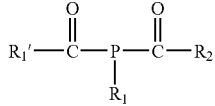 (I''')

by (1) reacting organic phosphorus halides of formula II''

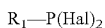 (II'')

with an alkali metal in a solvent in the presence of a proton source;

(2) subsequent reaction with an acid halide of formula III''

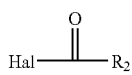 (III'')

(3) subsequent reaction with a second acid halide III'''

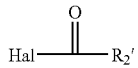 (III''')

wherein

R₁ is as defined in claim 1 and

R₂ and R₂' independently of one another are as defined in claim 1 under R₂ with the proviso that R₂ is not equal R₂', Hal is as defined in claim 1.

11. A process according to claim 1 for the preparation of mono acylated phosphanes of the formula VI and VI'

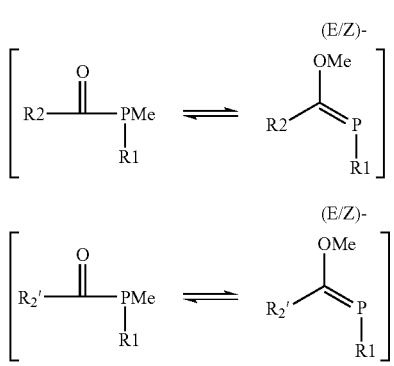

by (1) reacting organic phosphorus halides of formula II''

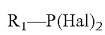 (II'')

with an alkali metal in a solvent in the presence of a proton source;

(2) subsequent reaction with an acid halide of formula III'' or III'''

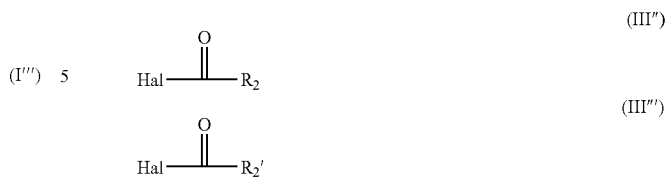

wherein R₁, R₂ are as defined in claim 1, R₂' is as defined in claim 1 under R₂ with the proviso that R₂ is not equal R₂' and Me is Li, Na, K or Mg in combination with Li.

12. A process according to claim 1, further comprising an additional step of oxiding the acylphosphane of formula (I) to prepare acylphosphane oxides or reacting the acylphosphane of formula (I) with sulfur to prepare acylphosphane sulfides of formula IV

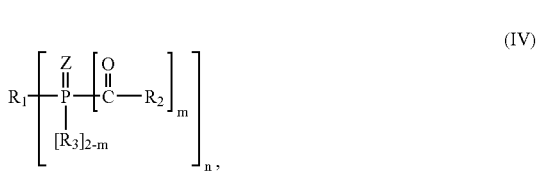 (IV)

wherein

R₁, R₂, R₃, n and m are as defined in claim 1, and Z is O or S.

13. A process according to claim 4, wherein the secondary and tertiary $C_3$-$C_{18}$ alcohols are selected from the group consisting of t-butanol, t-amyl-alcohol, 3-methyl-3-pentanol, 3-ethyl-3-pentanol, triphenylmethanol, 3,7-dimethyl-3-octanol, 2-methyl-1-phenyl-2-propanol, 2-methyl-4-phenyl-2-butanol, fenchyl alcohol, 2,4-dimethyl-3-pentanol, 1-dimethylamino-2-propanol or Hexylene glycol.

14. A process according to claim 5, wherein metallation is carried out in the presence of catalytic amounts of Na, K or Li sterically hindered alcoholates or sterically hindered alcohols.

15. A process according to claim 7, wherein the polyamine is N,N,N',N'-tetramethylethylenediamine.

16. A process according to claim 12, wherein a monoacylphosphane of formula I'

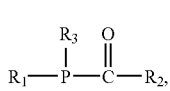 (I')

is oxidized or reacted sulfur.

17. A process according to claim 12, wherein a symmetric bisacylphosphane of formula I''

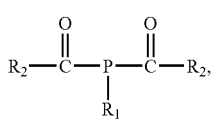 (I'')

is oxidized or reacted sulfur.

18. A process according to claim 12, wherein an unsymmetric bisacylphosphane of formula I'''

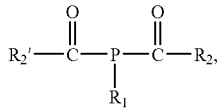

(I''')

is oxidized or reacted sulfur.

19. A process for the preparation of acylphosphanes of formula I

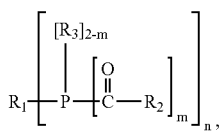

(I)

wherein
n and m are each independently of the other 1 or 2;
$R_1$, if n=1, is
$C_1$-$C_{18}$alkyl, $C_2$-$C_{18}$alkyl which is interrupted by one or several non-successive O atoms,
phenyl-$C_1$-$C_4$alkyl, $C_2$-$C_8$alkenyl, phenyl, naphthyl, biphenyl, $C_5$-$C_{12}$cycloalkyl or a 5- or 6-membered O-, S- or N-containing heterocyclic ring, the radicals phenyl, naphthyl, biphenyl, $C_5$-$C_{12}$cycloalkyl or the 5- or 6-membered O-, S- or N-containing heterocyclic ring being unsubstituted or substituted by one to five halogen, $C_1$-$C_8$alkyl, $C_1$-$C_8$alkylthio, $C_1$-$C_8$alkoxy and/or —N($R_8$)$_2$;
$R_1$, if n=2, is
$C_1$-$C_{18}$alkylene, $C_2$-$C_{18}$alkylene which is interrupted by one or several non-successive O atoms; or $R_1$ is $C_1$-$C_6$alkylene which is substituted by $C_1$-$C_4$alkoxy, phenyl, $C_1$-$C_4$alkylphenyl, phenyl-$C_1$-$C_4$alkyl or $C_1$-$C_6$alkoxyphenyl; or $R_1$ is phenylene or xylylene, which radicals are unsubstituted or substituted by one to three $C_1$-$C_4$alkyl and/or $C_1$-$C_4$alkoxy, or $R_1$ is a

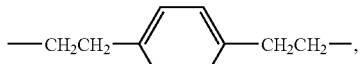

or

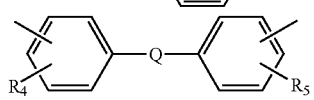

group;
$R_2$ is $C_1$-$C_{18}$alkyl, $C_3$-$C_{12}$cycloalkyl, $C_2$-$C_{18}$alkenyl, phenyl-$C_1$-$C_4$alkyl, phenyl, naphthyl, biphenyl or a 5- or 6-membered O-, S- or N-containing heterocyclic ring, the radicals phenyl, naphthyl, biphenyl or the 5- or 6-membered O-, S- or N-containing heterocyclic ring being unsubstituted or substituted by one to five halogen, $C_1$-$C_8$alkyl, $C_1$-$C_8$alkoxy and/or $C_1$-$C_8$alkylthio;
$R_3$ is $C_1$-$C_{18}$alkyl, $C_2$-$C_{18}$alkyl which is interrupted by one or several non-successive O atoms or which is interrupted by —CO—, —COO—, —OCO—, —OCOO—, —CO—N($R_9$)—, —N($R_9$)—CO—, —N($R_9$)—CO—N($R_9$)—, —N($R_9$)—COO—; $C_1$-$C_{18}$alkyl substituted by —O$R_{10}$, —OCO—$R_{10}$, —COO—$R_{10}$, —N($R_9$)—CO—$R_{10}$, —CO—N($R_9$)—$R_{10}$, —C($R_{11}$)=C($R_{12}$)—CO—O$R_{10}$ or —C($R_{11}$)=C($R_{12}$)-phenyl;
$C_2$-$C_{12}$alkenyl or $C_2$-$C_{12}$alkenyl which is interrupted by one or several non-successive O atoms;
phenyl-$C_1$-$C_4$alkyl, phenyl, naphthyl, biphenyl, $C_5$-$C_{12}$cycloalkyl or a 5- or 6-membered O-, S- or N-containing heterocyclic ring, the radicals phenyl, naphthyl, biphenyl, $C_5$-$C_{12}$cycloalkyl or the 5- or 6-membered O-, S- or N-containing heterocyclic ring being unsubstituted or substituted by one to five halogen, $C_1$-$C_8$alkyl, $C_1$-$C_8$alkylthio $C_1$-$C_8$alkoxy and/or —N($R_8$)$_2$; or $R_3$ is —CO—O$R_9$ or —CO—N($R_9$)$_2$;
Q is a single bond, $CR_6R_7$, —O— or —S—;
$R_4$ and $R_5$ are each independently of the other hydrogen, $C_1$-$C_4$alkyl or $C_1$-$C_4$alkoxy;
$R_6$ and $R_7$ are each independently of the other hydrogen or $C_1$-$C_4$alkyl;
$R_8$ is $C_1$-$C_{18}$ alkyl, $C_2$-$C_{18}$ alkyl which is interrupted by one or several non-successive O-atoms; or —N($R_8$)$_2$ forms a 5- or 6-membered O-, S- or N-containing heterocyclic ring;
$R_9$ is hydrogen, $C_1$-$C_{18}$alkyl, $C_2$-$C_{18}$alkyl which is interrupted by one or several non-successive O atoms, $C_3$-$C_{12}$-cycloalkyl, $C_2$-$C_{18}$-alkenyl, phenyl-$C_1$-$C_4$-alkyl, phenyl, naphthyl, pyridyl, the radicals phenyl, naphthyl or pyridyl being unsubstituted or substituted by one to five $C_1$-$C_8$-alkyl, $C_1$-$C_8$-alkoxy, $C_1$-$C_8$-alkylthio and/or halogen; or —N($R_9$)$_2$ forms a 5- or 6-membered O-, S- or N-containing heterocyclic ring;
$R_{10}$ is $C_1$-$C_{18}$alkyl, $C_2$-$C_{18}$alkyl which is interrupted by one or several non-successive O-atoms, $C_3$-$C_{12}$-cycloalkyl, phenyl-$C_1$-$C_4$-alkyl, $C_2$-$C_{18}$-alkenyl, phenyl, naphthyl or biphenyl, the radicals phenyl-$C_1$-$C_4$-alkyl, phenyl, naphthyl or biphenyl being unsubstituted or substituted by one to five $C_1$-$C_8$-alkyl, $C_1$-$C_8$-alkoxy, $C_1$-$C_8$-alkylthio and/or halogen;
$R_{11}$ is hydrogen or $C_1$-$C_4$-alkyl;
$R_{12}$ is hydrogen or $C_1$-$C_4$-alkyl;
by
($_1$) reacting diphospanes of the formula $(R_1)_2$—P—P$(R_1)_2$ or polyphosphanes of the formula $[R_1P]n$,
wherein n is $\geq$3 and $R_1$ is any group as defined for $R_1$ above with an alkali metal in a solvent in the presence of a proton source,
(2) followed by the reaction with acid halides of formula III

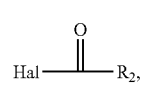

(III)

and/or by reaction with electrophilic compounds $R_3$-Hal, wherein $R_2$, $R_3$ and Hal have the meaning cited above.

* * * * *

UNITED STATES PATENT AND TRADEMARK OFFICE
CERTIFICATE OF CORRECTION

PATENT NO.        : 7,439,401 B2                                          Page 1 of 1
APPLICATION NO.   : 10/564711
DATED             : October 21, 2008
INVENTOR(S)       : Reinhard H. Sommerlade et al.

It is certified that error appears in the above-identified patent and that said Letters Patent is hereby corrected as shown below:

On title page

Item (75) should read:

-- (75) Inventors: Reinhard H. Sommerlade, Neuenburg am Rhein (DE); Souâd Boulmaâz, Birsfelden (CH); Jean-Pierre Wolf, Maisprach (CH); Jens Geier, Wuppertal (CH); Hansjörg Grützmacher, Dielsdorf (CH); Markus Scherer, Beromünster (CH); Hartmut Schönberg, Kilchberg (CH); Daniel Stein, Seelze (DE); Peter Murer, Allschwil (CH); Stephan Burkhardt, Gelterkinden (CH) --.

Signed and Sealed this

Twenty-fourth Day of February, 2009

JOHN DOLL
*Acting Director of the United States Patent and Trademark Office*